(12) United States Patent
Georgakoudi et al.

(10) Patent No.: US 8,380,268 B2
(45) Date of Patent: Feb. 19, 2013

(54) SYSTEM AND METHODS OF FLUORESCENCE, REFLECTANCE AND LIGHT SCATTERING SPECTROSCOPY FOR MEASURING TISSUE CHARACTERISTICS

(75) Inventors: Irene Georgakoudi, Acton, MA (US); Michael S. Feld, Newton, MA (US); Qingguo Zhang, Medford, MA (US); Markus G. Mueller, Erlenbach (DE)

(73) Assignee: Massachusetts Institute of Technology, Cambridge, MA (US)

( * ) Notice: Subject to any disclaimer, the term of this patent is extended or adjusted under 35 U.S.C. 154(b) by 30 days.

(21) Appl. No.: 11/166,798

(22) Filed: Jun. 24, 2005

(65) Prior Publication Data

US 2005/0288593 A1    Dec. 29, 2005

Related U.S. Application Data

(63) Continuation of application No. 10/052,583, filed on Jan. 18, 2002, now Pat. No. 6,912,412, which is a continuation-in-part of application No. 09/766,879, filed on Jan. 19, 2001, now Pat. No. 6,697,652.

(51) Int. Cl.
*A61B 5/00* (2006.01)

(52) U.S. Cl. .......................... 600/310; 600/476

(58) Field of Classification Search ................... 128/634, 128/665; 356/432, 369, 342, 364, 367, 340; 600/310, 473, 476, 477, 478, 407, 178, 160, 600/314; 382/128, 190; 395/21, 924

See application file for complete search history.

(56) References Cited

U.S. PATENT DOCUMENTS

| | | | |
|---|---|---|---|
| 4,768,513 A | | 9/1988 | Suzuki |
| 4,773,097 A | | 9/1988 | Suzaki et al. |
| 5,199,431 A | * | 4/1993 | Kittrell et al. ............... 600/477 |
| 5,201,318 A | | 4/1993 | Rava et al. |
| 5,280,788 A | | 1/1994 | Janes et al. |
| 5,304,173 A | | 4/1994 | Kittrell et al. |
| 5,318,024 A | | 6/1994 | Kittrell et al. |
| 5,345,941 A | | 9/1994 | Rava et al. |
| 5,349,954 A | * | 9/1994 | Tiemann et al. ............. 600/342 |
| 5,419,312 A | * | 5/1995 | Arenberg et al. ............ 600/108 |
| 5,419,323 A | | 5/1995 | Kittrell et al. |
| 5,421,337 A | | 6/1995 | Richards-Kortum et al. |
| 5,421,339 A | * | 6/1995 | Ramanujam et al. ......... 600/477 |
| 5,441,053 A | * | 8/1995 | Lodder et al. ................ 600/473 |

(Continued)

FOREIGN PATENT DOCUMENTS

| | | |
|---|---|---|
| EP | 0 449 883 | 10/1991 |
| JP | 2002-95624 | 4/2002 |

(Continued)

OTHER PUBLICATIONS

Yang et al., "Feasibility of field-based light scattering spectroscopy," Journal of Biomedical Optics 5 (2), (Apr. 2000), pp. 138-143.

(Continued)

*Primary Examiner* — Long V. Le
*Assistant Examiner* — Lawrence N Laryea
(74) *Attorney, Agent, or Firm* — McCarter & English LLP

(57) ABSTRACT

The present invention utilizes a plurality of spectroscopic systems and methods to measure characteristics of tissue useful in the diagnosis of disease. In a preferred embodiment, a combination of fluorescence, reflectance and light scattered spectra can be measured and processed to provide biochemical, architectural and morphological state of tissue. The methods and systems can be used particularly in the early detection of carcinoma within tissue in vivo and in vitro.

31 Claims, 21 Drawing Sheets

U.S. PATENT DOCUMENTS

| | | | |
|---|---|---|---|
| 5,452,723 A | | 9/1995 | Wu et al. |
| 5,562,100 A | | 10/1996 | Kittrell et al. |
| 5,582,168 A | | 12/1996 | Samuels et al. |
| 5,697,373 A | | 12/1997 | Richards-Kortum et al. |
| 5,822,072 A | | 10/1998 | Dai et al. |
| 5,833,612 A | * | 11/1998 | Eckhouse et al. ............. 600/476 |
| 5,842,995 A | * | 12/1998 | Mahadevan-Jansen et al. ............................. 600/473 |
| 5,920,399 A | * | 7/1999 | Sandison et al. ............... 356/418 |
| 6,008,889 A | | 12/1999 | Zeng et al. |
| 6,021,344 A | | 2/2000 | Lui et al. |
| 6,066,245 A | * | 5/2000 | Trost ............................. 204/461 |
| 6,069,689 A | | 5/2000 | Zeng et al. |
| 6,091,984 A | * | 7/2000 | Perelman et al. ............. 600/476 |
| 6,128,525 A | | 10/2000 | Zeng et al. |
| 6,135,965 A | * | 10/2000 | Tumer et al. ................... 600/476 |
| 6,201,989 B1 | | 3/2001 | Whitehead et al. |
| 6,321,111 B1 | | 11/2001 | Perelman et al. |
| 6,353,226 B1 | * | 3/2002 | Khalil et al. .................. 600/310 |
| 6,377,841 B1 | * | 4/2002 | Lin et al. ........................ 600/477 |
| 6,404,497 B1 | | 6/2002 | Backman et al. |
| 6,537,211 B1 | * | 3/2003 | Wang et al. .................... 600/178 |
| 6,546,272 B1 | | 4/2003 | MacKinnon et al. |
| 6,571,118 B1 | * | 5/2003 | Utzinger et al. .............. 600/476 |
| 6,697,652 B2 | | 2/2004 | Georgakoudi et al. |
| 6,826,424 B1 | | 11/2004 | Zeng et al. |
| 6,898,458 B2 | | 5/2005 | Zeng et al. |
| 6,903,813 B2 | * | 6/2005 | Jung et al. ........................ 356/73 |
| 6,912,412 B2 | * | 6/2005 | Georgakoudi et al. ........ 600/310 |
| 7,115,841 B2 | | 10/2006 | Zeng et al. |
| 7,190,452 B2 | | 3/2007 | Zeng et al. |
| 7,235,045 B2 | * | 6/2007 | Wang et al. .................... 600/109 |
| 7,253,894 B2 | | 8/2007 | Zeng et al. |
| 7,620,212 B1 | * | 11/2009 | Allen et al. .................... 382/115 |
| 2002/0093563 A1 | | 7/2002 | Cline et al. |
| 2002/0156380 A1 | * | 10/2002 | Feld et al. ..................... 600/473 |
| 2003/0231309 A1 | * | 12/2003 | Fulghum et al. .............. 356/338 |
| 2004/0044287 A1 | * | 3/2004 | Lin et al. ....................... 600/475 |

FOREIGN PATENT DOCUMENTS

| | | |
|---|---|---|
| WO | WO 99/18845 | 4/1999 |
| WO | WO 00/42912 | 7/2000 |
| WO | WO 01/34031 | 5/2001 |

OTHER PUBLICATIONS

Perelman et al., "Observation of Periodic Fine Structure in Reflectance from Biological Tissue: A New Technique for Measuring Nuclear Size Distribution," The American Physical Society, 80 (3), (Jan. 1998), pp. 627-630.

Backman et al., "Detection of preinvasive cancer cells," Nature 406, (Jul. 2000), pp. 35-36.

Zonios et al., "Diffuse reflectance spectroscopy of human adenomatous colon polyps in vivo," Applied Optics, vol. 38 (31), (Nov. 1999), pp. 6628-6637.

Panjehpour et al., "Endoscopic Fluorescence Detection of High-Grade Dysplasia in Barrett's Esophagus," Gastroenterology 111 (1996), pp. 93-101.

Wallace et al., "Endoscopic Detection of Dysplasia in Patients With Barrett's Esophagus Using Light-Scattering Spectroscopy," Gastroenterology 119 (2000), pp. 677-682.

Zhang et al., "Turbidity-free fluorescence spectroscopy of biological tissue," Optics Letters, vol. 25 (19) (Oct. 2000), pp. 1451-1453.

Georgakoudi et al., "Fluorescence, reflectance and light scattering spectroscopy for evaluating dysplasia in patients with Barrett's esophagus," Gastroenterology, pp. 1-15, downloaded Dec. 6, 2000 from www.gastro-central.org.

Yang et al., "Phase Dispersion Optical Tomography," Optics Letters (2000), pp. 1-12.

"Tri-Modal Spectroscopy—A New Approach to Spectroscopic Detection of Cervical Neoplasia In Vivo," (abstract), 1 page.

Georgakoudi et al., "Spectroscopy for Detection of Cancer," presented at the APS Mar. 2001 meeting in Seattle, WA, 1 page.

Richards-Kortum et al, "A One-Layer Model of Laser-Induced Fluorescence for Diagnosis of Disease in Human Tissue: Applications to Atherosclerosis," IEEE Transactions on Biomedical Engineering, vol. 36 (12), Dec. 1989, 12 pages.

\* cited by examiner

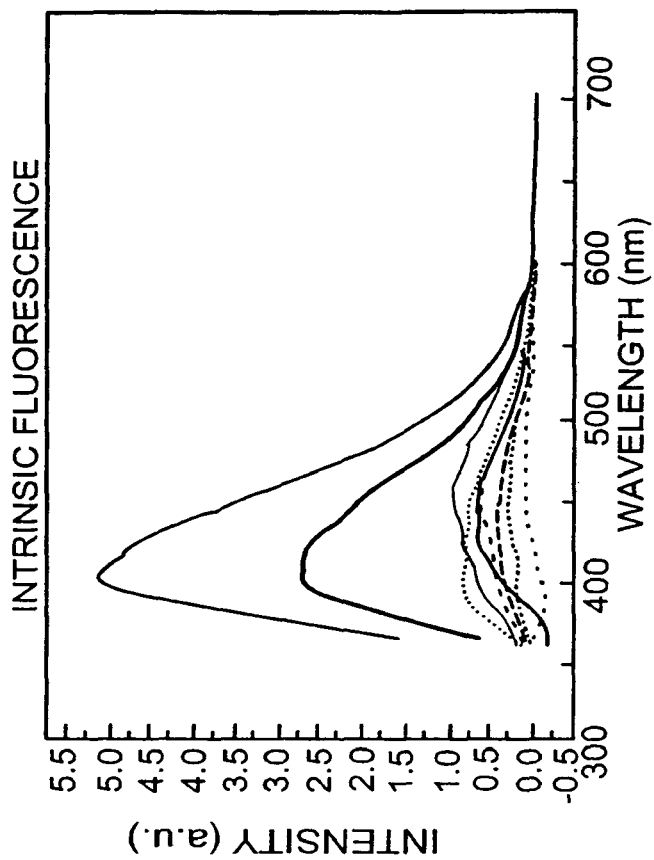
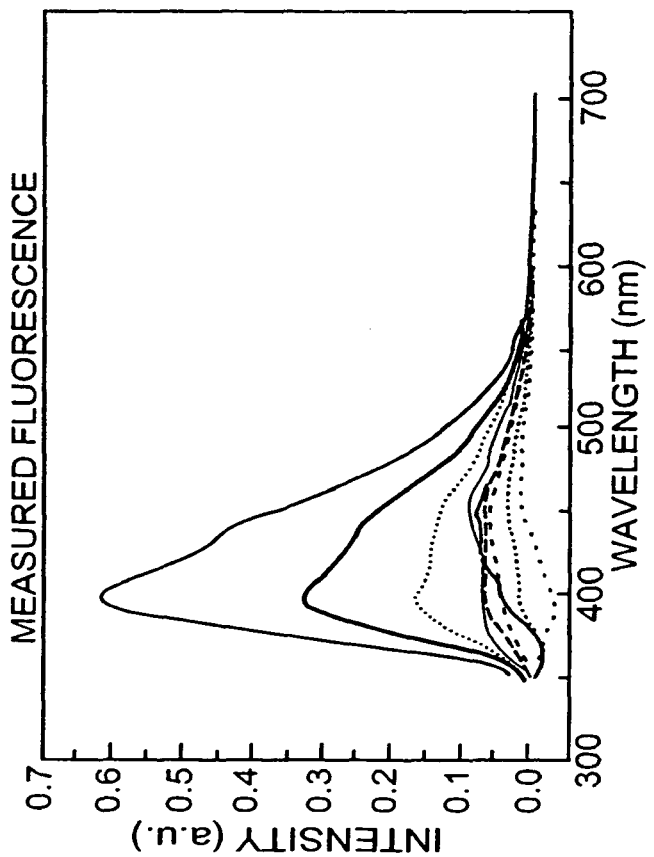
FIG. 9A
FIG. 9B

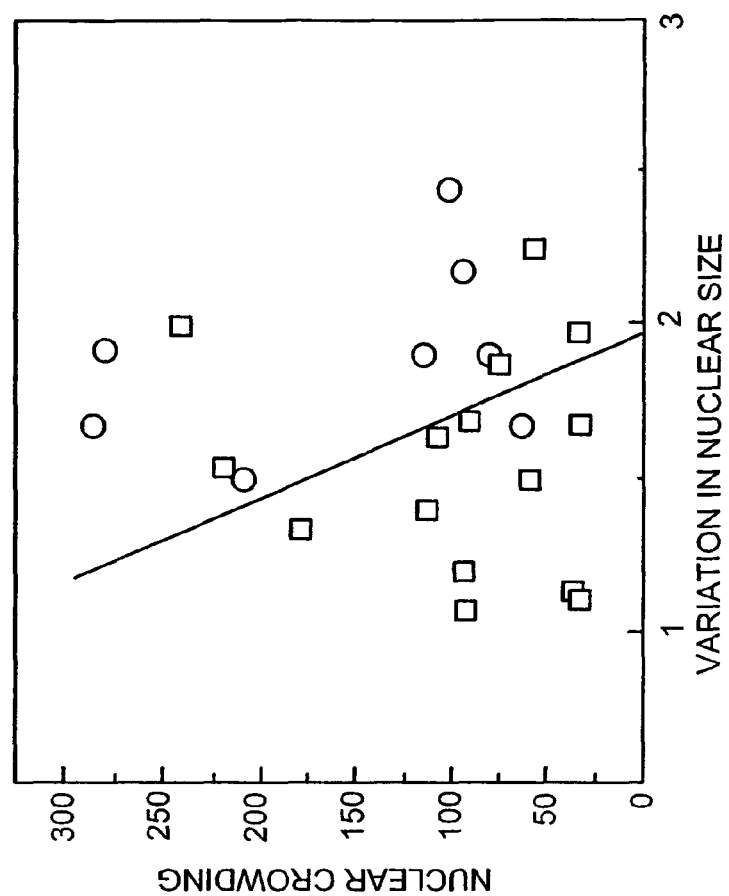
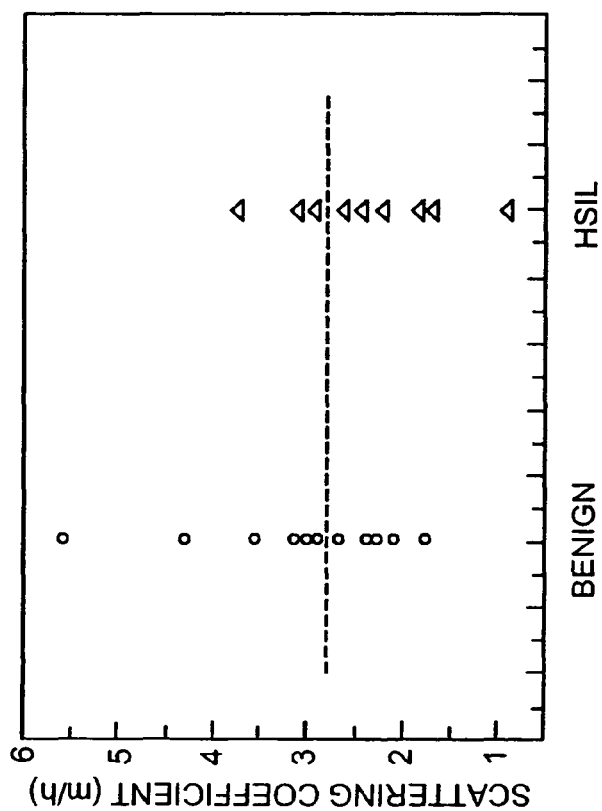
FIG. 11B
FIG. 11A

SYSTEM AND METHODS OF FLUORESCENCE, REFLECTANCE AND LIGHT SCATTERING SPECTROSCOPY FOR MEASURING TISSUE CHARACTERISTICS

CROSS REFERENCES TO RELATED APPLICATIONS

The present application is a continuation of U.S. patent application Ser. No. 10/052,583 filed on Jan. 18, 2002, now U.S. Pat. No. 6,912,412, which is a continuation-in-part of U.S. patent application Ser. No. 09/766,879, filed Jan. 19, 2001, now U.S. Pat. No. 6,697,652. The entire contents of the above applications are incorporated herein by reference.

STATEMENT REGARDING FEDERALLY SPONSORED RESEARCH OR DEVELOPMENT

This invention was made with government support awarded by the National Institutes of Health under Grant Numbers 5-P41-RR02594-15 and 5-R01-CA53717-12. The government has certain rights in this invention.

BACKGROUND OF THE INVENTION

Adenocarcinoma of the lower esophagus develops almost exclusively in patients with Barrett's esophagus (BE), a condition characterized by the presence of metaplastic columnar epithelium. While the prognosis of patients diagnosed with adenocarcinoma is poor, the chances of successful treatment increase significantly if the disease is detected at the dysplastic stage. The surveillance of patients with BE for dysplasia is challenging in two respects. First, dysplasia is not visible during routine endoscopy. Thus, numerous random biopsies are required. Second, the histopathologic diagnosis of dysplasia is problematic, as there is poor inter-observer agreement on the classification of a particular specimen, even among expert gastrointestinal pathologists. Optical techniques, such as fluorescence, may significantly enhance the endoscopist's ability to detect these early dysplastic changes in BE. Indeed, fluorescence spectroscopy studies using exogenous fluorophores, such as Photofiin® and aminolevulinic-acid induced protoporphyrin IX, show that there is a significant difference between the measured red fluorescence of the carcinomatous and non-dysplastic tissue as a result of the preferential accumulation of the drug. Initial autofluorescence spectroscopy studies performed at 410 nm excitation report promising results for detecting high-grade dysplasia. However, focal high-grade and low-grade lesions could not be detected reliably. Thus a continuing need exists for further improvements in the optical measurements used to detect early stage carcinomas.

SUMMARY OF THE INVENTION

The present invention relates to a combination of spectroscopic systems that can improve the sensitivity and accuracy of measuring the state of tissue. For example, a plurality of different spectroscopic systems can be used to determine whether a region of tissue is normal, pre-cancerous or cancerous. In a preferred embodiment dysplasia detection in patients with Barrett's esophagus (BE) can be performed. In a preferred embodiment, fluorescence, reflectance and light scattering spectroscopies provide complementary information about the biochemical, architectural and morphological state of tissue and the corresponding changes that occur during the progression of disease, and in particular, of dysplasia.

In a preferred embodiment, the system has been developed for combining these three methods to provide for detection, mapping, and/or imaging of tissue. In particular, methods of processing the spectral or image data with a data processor programmed to perform an automated diagnostic routine is useful to provide the results of a plurality of different measurement modalities including fluorescence and light scattering spectroscopy. A further preferred embodiment of the invention utilizes a tri-modal system to guide a biopsy procedure.

Of importance in this system for real-time measurements is the simultaneous or near simultaneous collection of light from the same spot or region of interest. For example, the collection of light includes the collection of a measured fluorescence and reflectance spectra. The detected reflectance spectrum is processed to remove a diffusive background component. Once this is accomplished, then a component of the light that is periodic in wavelength is measured. This component arises from the light that is Mie-scattered by surface epithelial cell nuclei, for example. By analyzing the amplitude and frequency of the periodic structure, the density and size distribution of these nuclei can be extracted. For the reflectance, light scattered and fluorescence components to be properly correlated and used to assess a given region of interest, there is preferably substantial overlap of the excitation light for both the reflectance and fluorescence measurements. The reflected light is used to both correct the fluorescence spectrum and to generate a light scattered spectrum based on the use of the periodic structure contained therein. The apparatus delivers both excitation components to the region of interest through the same distal surface of the probe, preferably through the same optical fiber or collection of fibers.

The biopsy channel of an endoscope can be used to insert the fiber optic light delivery and collection system used to obtain measurements. Alternatively, a small diameter endoscope, 5 mm or less in diameter, for example, can include the light delivery and collection system suitable for many applications. A preferred embodiment of the system can use a single fiber system for delivery and collection, or alternatively, can employ a central delivery fiber and six collection fibers concentrically arranged around the delivery fiber. The proximal end of the light delivery and collection probe is optically coupled to both a broadband flash lamp and a monochromatic source such as a laser. A rotating filter or dye wheel can be used to rapidly switch the excitation wavelength over a selected range.

The need for using reflected light arises from the need to correct for the effects of hemoglobin absorption on the measured integrated tissue fluorescence intensity. The combination of fluorescence and reflectance spectroscopies can be applied to remove distortions introduced by scattering and absorption into the entire measured tissue fluorescence spectrum. The undistorted or modified fluorescence spectrum can serve as a sensitive indicator of tissue biochemistry, while reflectance and light scattering representations provide morphological information on tissue architecture and epithelial cell nuclei. The present invention can include the simultaneous use of all three spectroscopic methods for characterizing tissue and diagnosing disease. The following demonstrates that the combined use of all three techniques provides improved results as compared to the results of each technique individually, in terms of detecting not only high-grade, but also low-grade dysplastic changes in BE, for example.

In a preferred embodiment, a method of analyzing spectral data to measure a structure in a layer of tissue includes providing a light collection system to collect fluorescent and reflected light from the tissue at a plurality of wavelengths and detect the collected light. The method further includes forming a fluorescence representation and a scattered light representation as a function of wavelength from the detected light. The method includes determining a characteristic of the tissue layer with the fluorescent representation and the scattered light representation. The method includes using the scattered light representation to determine a size of a structure, for example, the nuclei of cells, within the tissue layer. A diffuse reflectance spectrum can be analyzed in a preferred embodiment. The method, in the preferred embodiment includes generating a lookup table with different sizes of scatterers. The fluorescence representation can be corrected to obtain an intrinsic fluorescence spectrum.

In a preferred embodiment of the present invention a method for analyzing tissue spectra includes acquiring a fluorescence spectrum, acquiring a reflectance spectrum and then processing the two to provide an intrinsic fluorescence spectrum, a diffuse reflectance spectrum and a light-scattering spectrum. The method includes determining a biophysical tissue characteristic from the intrinsic fluorescence spectrum, the diffuse reflectance spectrum and the light scattering spectrum. The method may include performing a discrimination analysis using the diagnostic parameters from the diffuse reflectance spectrum, the diagnostic parameters from the intrinsic fluorescence spectrum and the diagnostic parameters from the light scattered spectrum and then providing a diagnosis.

BRIEF DESCRIPTION OF THE DRAWINGS

FIGS. 9A-9D illustrate graphically the measured and intrinsic fluorescence spectra of normal squamous epithelium (solid line), benign biopsied sites (dashed lines) and high-grade SILs (dotted lines). Curves A and B show differences in the lineshape and intensity observed at 337 nm excitation. Curves C and D show intensity differences observed in the intrinsic fluorescence excited at 358 nm.

FIG. 11A shows reduced scattering coefficient at 400 nm for benign biopsied and high-grade dysplatic sites.

FIG. 11B shows nuclear crowding or total number of nuclei per mm$^2$ plotted as a function of the standard derivation of the nuclear size population for a particular site. The line is determined by logistic regression.

The foregoing and other objects, features and advantages of the invention will be apparent from the following more particular description of preferred embodiments of the invention, as illustrated in the accompanying drawings in which

DETAILED DESCRIPTION OF THE INVENTION

Figure 1:
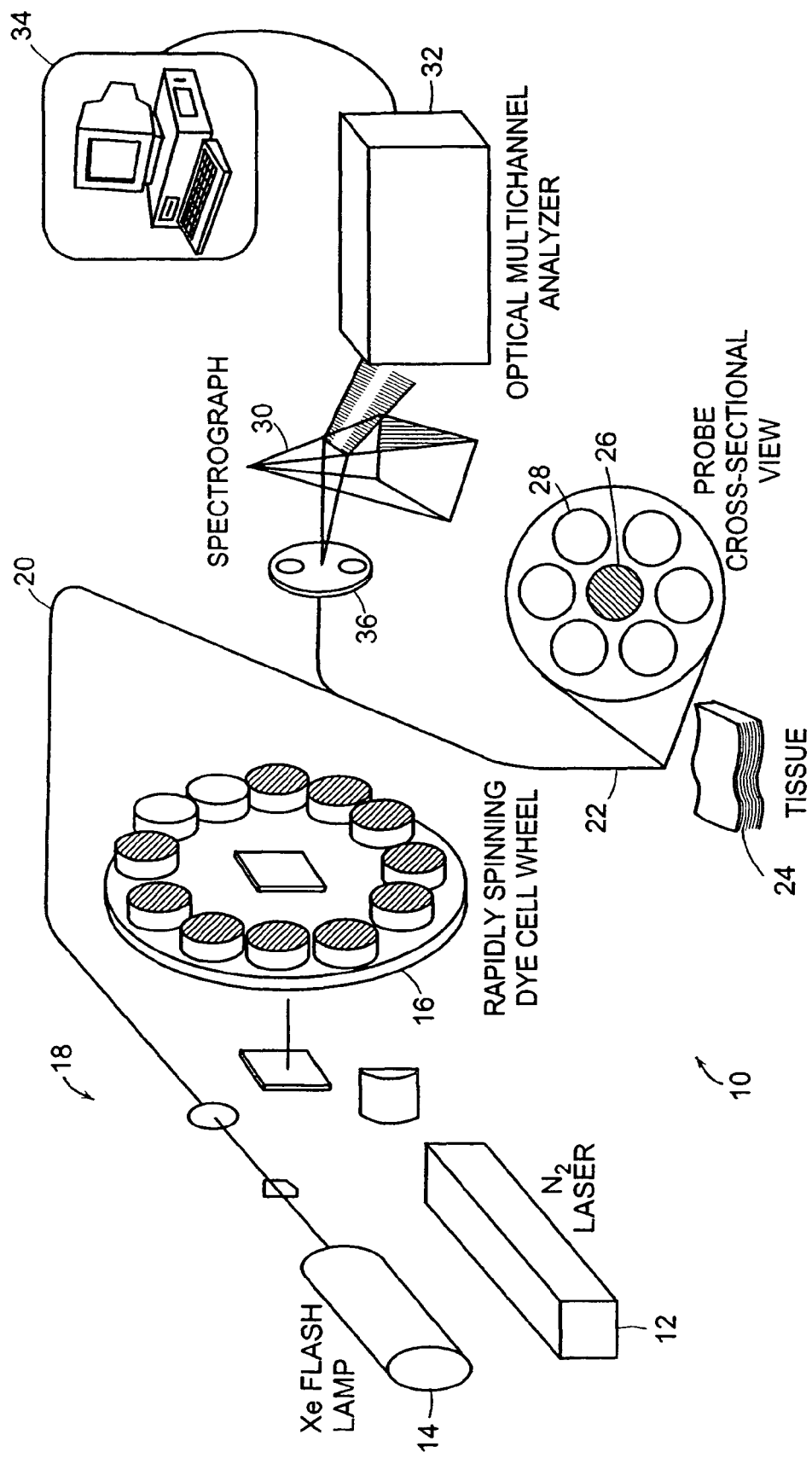
FIG. 1 schematically illustrates a preferred embodiment of a system for performing measurements in accordance with the invention.

Measurements are performed, for example, using a fast excitation-emission matrix (EEM) instrument 10 that has been described in greater detail in U.S. application Ser. No. 09/238,664, filed Jan. 26, 1999, the entire contents of which is incorporated herein by reference. The excitation light source of this fast-EEM system can include a nitrogen laser 12 emitting at 337 nm (Laser Science, Inc., Franklin, Mass.; Model: VSL-337MD) pumping 10 dye cuvettes precisely mounted on a rapidly rotating wheel 16. In this manner, in a preferred embodiment, eleven different excitation wavelengths are obtained between 337 and 620 nm and coupled using optical system 18 into the delivery fiber of a 1 mm diameter optical fiber probe 20. For the reflectance measurements, white light (350-700 nm) from a Xe flash lamp 14 (Perkin Elmer Optoelectronics, Salem, Mass.) is coupled into the same probe. Alternatively, for other embodiments involving measurements in the bladder, for example, a XeCl excimer laser emitting at 308 nm can be used. In a preferred embodiment, the probe is composed of six collection fibers 28 surrounding the central light delivery fiber 26, and it is covered with a protective, transparent optical shield at the distal end 22 as shown in FIG. 1.

During endoscopy, the probe is inserted into the accessory channel of the endoscope and brought into gentle contact with the tissue 24, thus providing a fixed delivery-collection geometry. The reflected and fluorescence light is collected by the probe and coupled to a spectrograph 30, analyzer 32, and detector 22. A second synchronized wheel 36 is used to block the fluorescence excitation wavelength. The average of three sets of spectra from each site is used for analysis using a data processing system 34. Immediately following data acquisition, the probe is removed and a slight demarcation remains on the tissue for 30 to 60 seconds as a result of the probe contact. This endoscopically apparent marker is used as a guide for taking a biopsy from the same site at which spectra were acquired. The biopsy specimen is interpreted and classified by a gastrointestinal pathologist. If a dysplastic lesion is suspected, the specimen is reviewed and the diagnosis confirmed by a second gastrointestinal pathologist, in accordance with the standard of care. Data has been analyzed from 26 non-dysplastic Barrett's esophagus sites (9 patients), 7 low-grade (4 patients) and 7 high-grade (5 patients) dysplastic sites.

Three types of spectroscopic information are acquired, preferably in less than one second in a preferred embodiment. Fluorescence spectra at eleven different excitation wavelengths, reflectance spectra and light scattering spectra are obtained. Each type of spectrum can be analyzed in a manner that provides information about biochemical and morphological changes that occur during dysplastic transformation. Fluorescence spectroscopy can provide valuable information about changes that take place in tissue biochemistry during the development of dysplasia. However, the measured tissue fluorescence spectra can be distorted significantly by unrelated scattering and absorption events. To remove these distortions, the fluorescence spectra are analyzed in combination with information from the corresponding reflectance spectra. The success of this procedure is predicated on the fact that the fluorescence and reflectance spectra collected from a specific site or region of interest using the same light delivery/collection geometry undergo similar distortions. By extracting the intrinsic (undistorted) tissue fluorescence, changes in tissue biochemistry may be isolated in a more sensitive and specific manner.

Principal component analysis and logistic regression is employed to determine the correlation between spectral features of the intrinsic fluorescence and histopathological diagnosis. To analyze this relatively small data set in an unbiased manner, "leave-one-out" cross-validation can be used. Specifically, the principal components of the intrinsic fluorescence spectra that described the spectral features that change during the progression of dysplasia are selected. The corresponding scores (the coefficients describing the contributions of the principal components to the overall spectra) can be used to determine the ability of the system to distinguish (a) high-grade dysplasia from low-grade dysplastic and non-dysplastic Barrett's esophagus (BE), and (b) dysplastic (low- and high-grade) from non-dysplastic Barrett's esophagus (BE). To achieve that in an unbiased manner, the following procedure can be performed. The scores from a particular site are eliminated, and logistic regression is used to form a decision surface that classifies the remaining sites in a manner that optimizes agreement with the histopathological classification. The resulting decision surface may be then used to classify the excluded site. This process can be repeated for each of the sites. This method provides use of a relatively small data set to validate the performance of a decision surface without bias. The decision surface varied minimally during this procedure, indicating the reliability of the technique. Sensitivity and specificity values can be determined by comparing the spectroscopic classification with histopathology. Statistical analysis may be performed using Matlab statistic software (The Math Works, Inc, Natick, Mass.) in accordance with a preferred embodiment.

The measured reflectance spectra can be analyzed using a representation based on diffusion theory which expresses the reflected light as a function of the absorption ($\mu_a(\lambda)$) and reduced scattering $\mu_s'(\lambda)$) coefficients of tissue. This analysis provides information about the architecture and morphology of mainly the connective tissue, i.e. the lamina propria and the submucosa, as the collected light originates within 500-700 µm from the tissue surface. The diagnostic value of the resulting tissue scattering coefficient values can be determined by correlating the results of logistic regression and cross-validation with histopathological classification, as in the intrinsic fluorescence case.

A small fraction (2-5%) of the detected reflected light originates from light collected by the probe after being scattered only once by the tissue. This method described generally herein as light scattering spectroscopy is described in greater detail in U.S. Pat. No. 6,091,984, issued on Jul. 18, 2000, the entire contents of which is incorporated herein by reference. Additional methods for measuring tissue structure are described in International Application No. PCT/US98/2145, filed on Oct. 9, 1998 designating the United States, the entire contents of which is also incorporated herein by reference. The intensity of this singly-scattered light contains a component which is periodic in inverse wavelength, the magnitude and frequency of which depends on the number and size of the nuclei in the epithelial cell layer. This periodic signal is analyzed to determine the number and size of epithelial cell nuclei corresponding to a particular site. Logistic regression and cross-validation are then used to compare the spectroscopic classification with that of histopathology. To optimize sensitivity and specificity, the posterior probability threshold for separating high-grade dysplasia from non-high-grade dysplasia sites is set to 0.3 in one preferred embodiment.

Finally, results from all three spectroscopic techniques are combined to determine whether the number of correctly classified sites can be improved. Specifically, a site is assigned a classification that is consistent with results from at least two of the three analysis methods, and this classification is compared to histopathology.

Figure 2B:
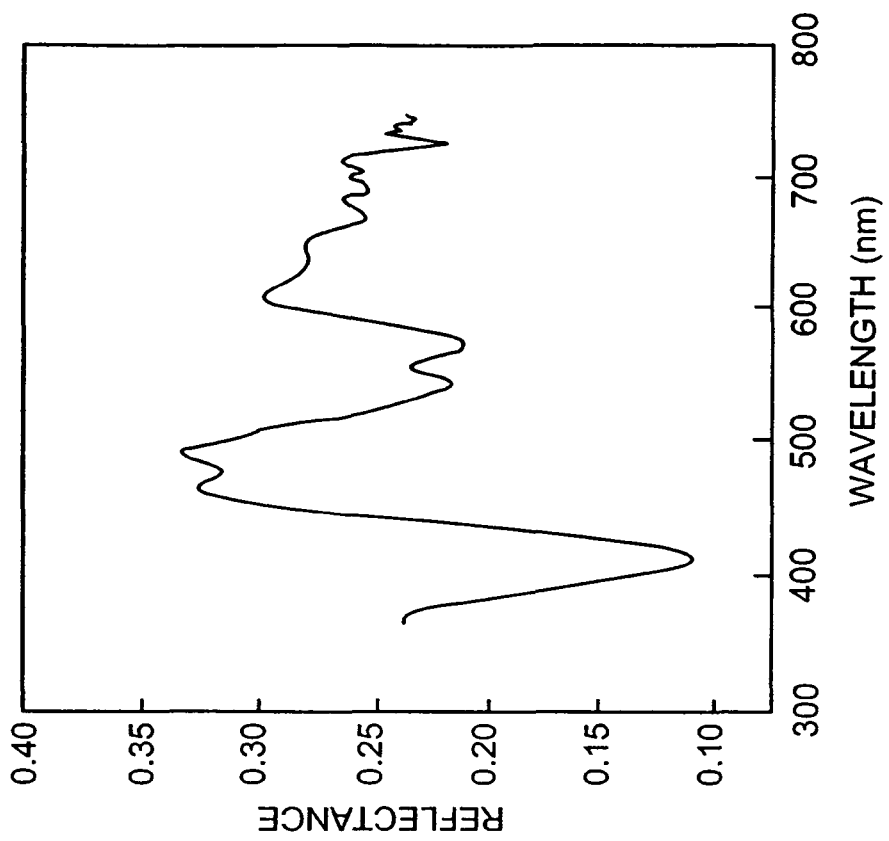
FIG. 2B illustrates graphically the corresponding reflectance spectrum in accordance with the fluorescence spectrum illustrated in FIG. 2A.
Figure 2A:
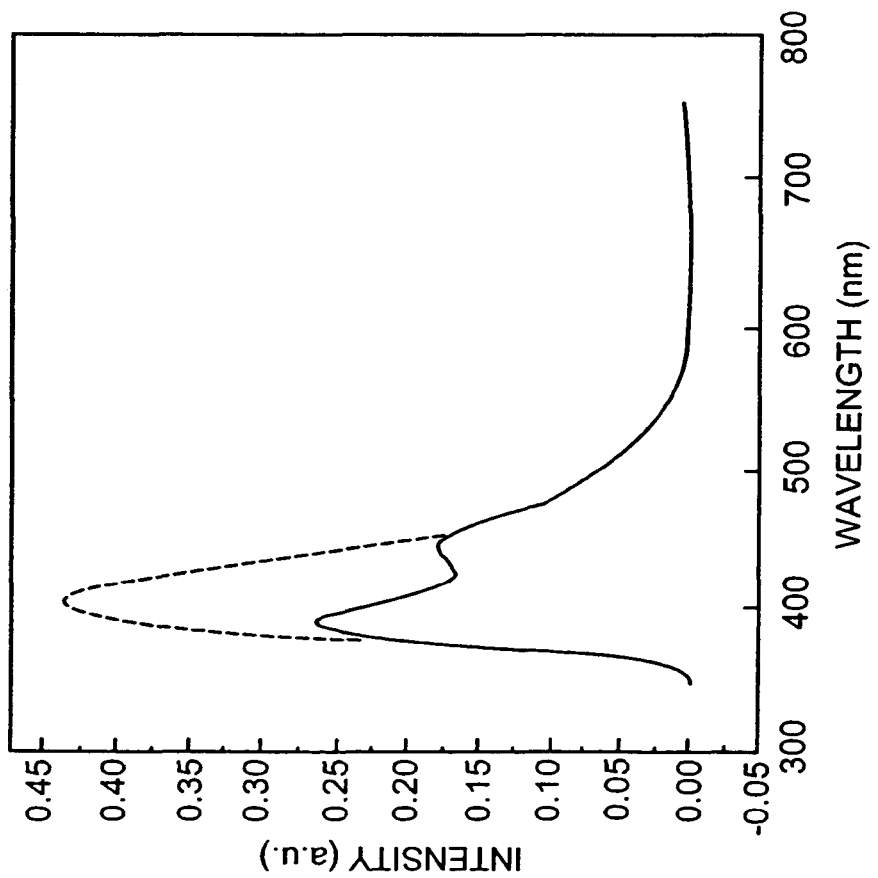
FIG. 2A illustrates graphically fluorescence from a non-dysplastic Barrett's esophagus site, 337 nm excitation wherein the measured spectrum is the solid line; extracted intrinsic fluorescence is the dashed line.

FIG. 2A shows a typical fluorescence spectrum excited with 337 nm light from a non-dysplastic Barrett's esophagus (BE) site (solid line). There are two peaks, which can be attributed to the presence of two different tissue fluorophores. Note that the fluorescence intensity decrease between these two peaks occurs at the wavelength range in which hemoglobin absorbs light very efficiently. The effects of hemoglobin absorption are observed in the corresponding reflectance spectrum, which exhibits minima at approximately 420, 540 and 580 nm, corresponding to oxy-hemoglobin absorption peaks (FIG. 2B). When the measured fluorescence spectrum of FIG. 2A is processed in combination with the corresponding reflectance spectrum of FIG. 2B as discussed herein, the intrinsic (undistorted) tissue fluorescence spectrum at the particular excitation wavelength is obtained (FIG. 2A, dashed line). Note that this spectrum consists of a single broad peak.

Figure 3B:
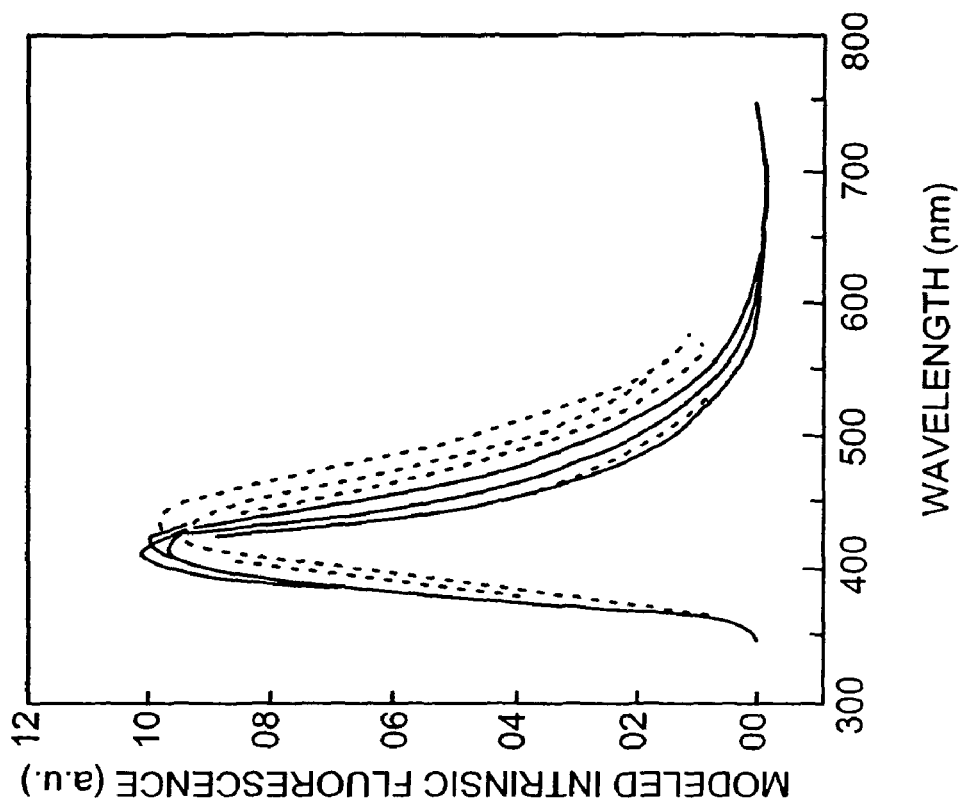
FIGS. 3A-3D illustrate the fluorescence spectra from non-dysplastic (solid lines), low-grade (dashed-lines) and high-grade dysplastic (dotted lines) Barrett's esophagus (BE) sites. The measured and corresponding extracted intrinsic fluorescence for excitation at 337 nm ((A) and (B)) and 397 nm ((C and (D)) are shown. Spectra are normalized to their peak intensities. Note the significant lineshape changes. The mean±standard deviation values are displayed for each category.
Figure 3A:
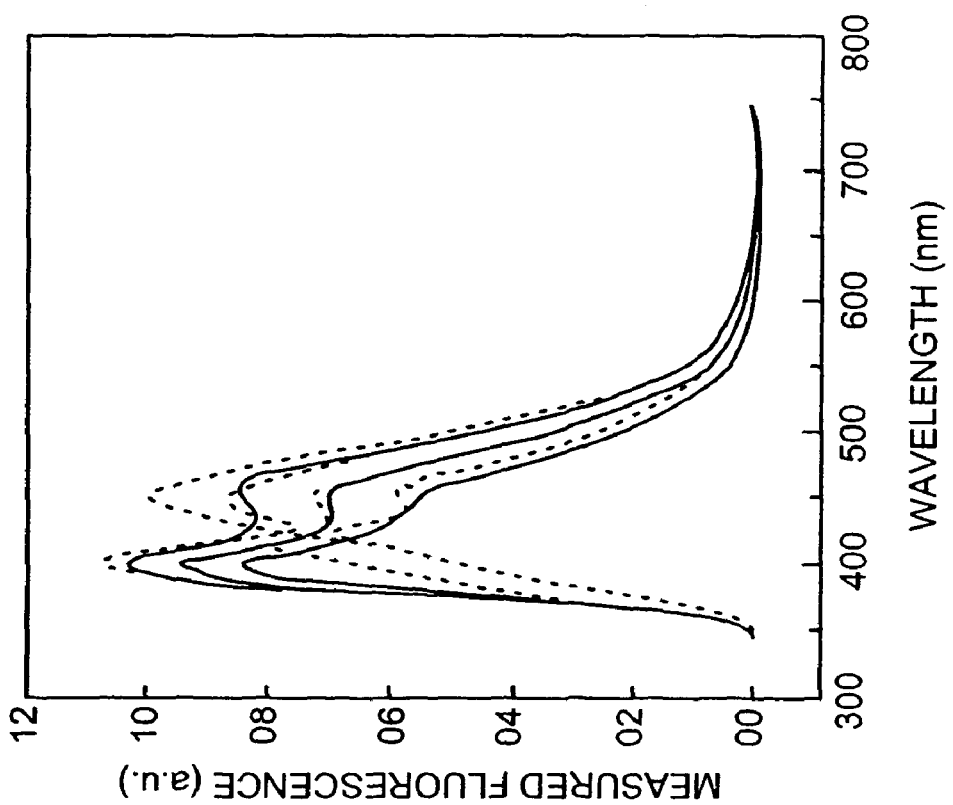
Figure 3D:
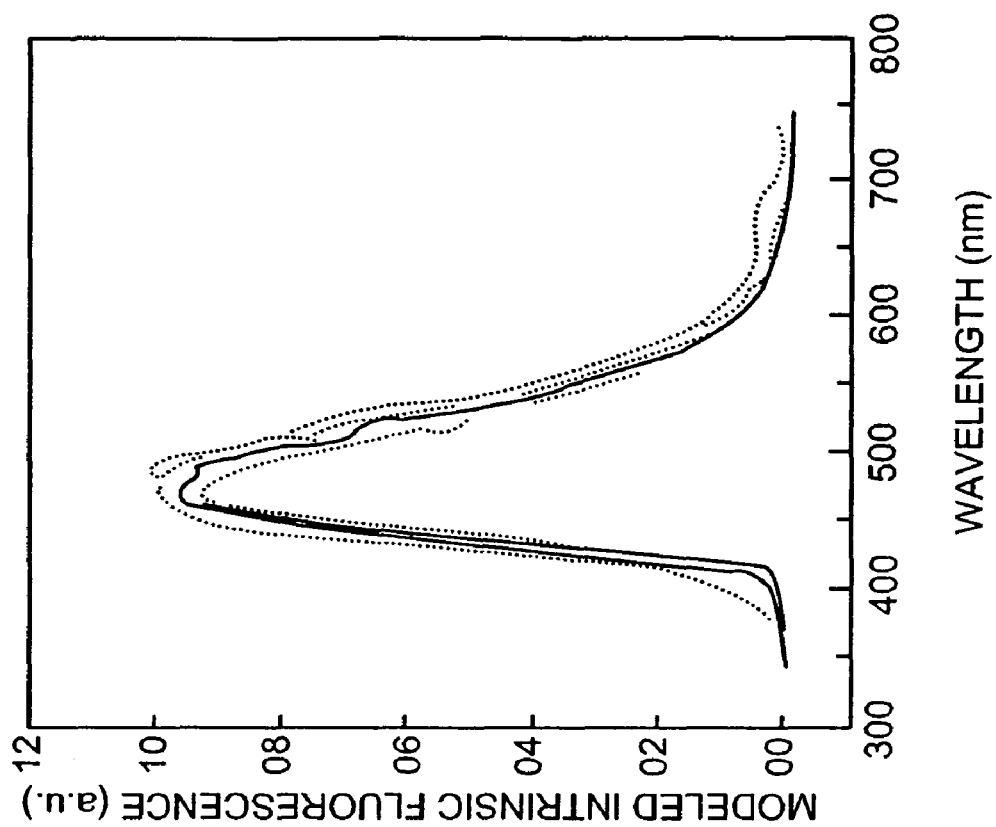
Figure 3C:
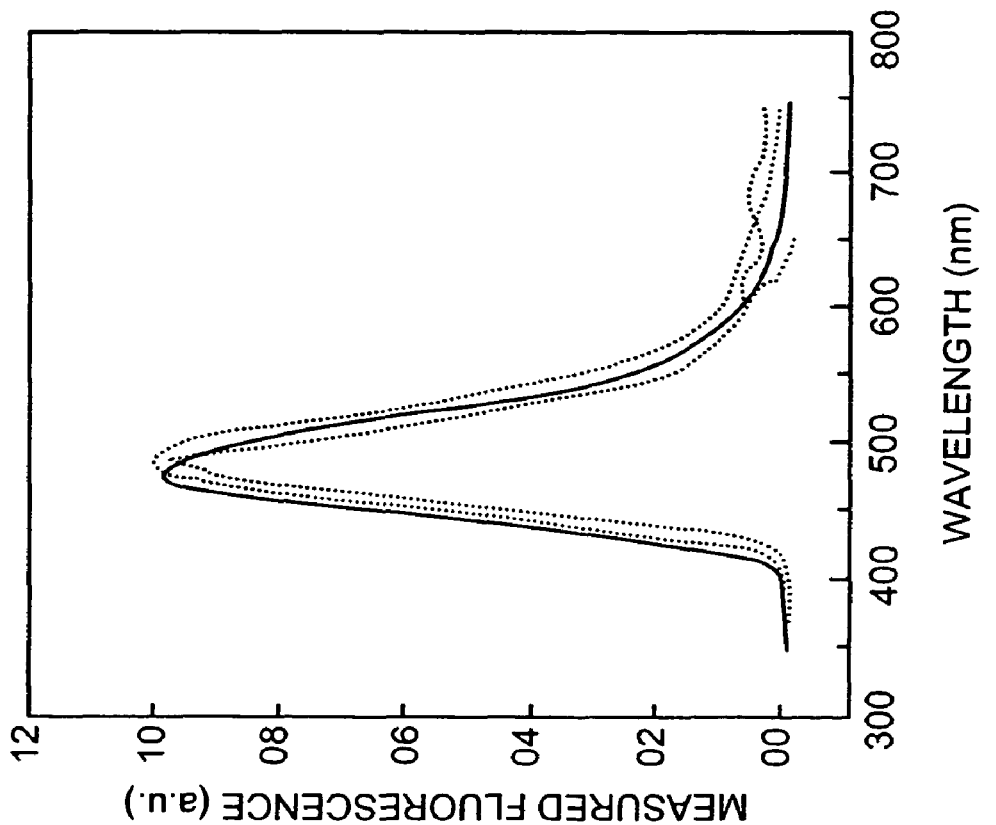

Significant differences are observed in the representation of intrinsic tissue fluorescence of non-dysplastic and dysplastic Barrett's esophagus (BE) sites excited at 337 nm (FIGS. 3A and 3B) and 397 nm (FIGS. 3C, 3D). At 337 nm excitation the lineshape of the dysplastic sites broadens and shifts to the red region of the spectrum during the progression from non-dysplastic, to low-grade, to high-grade dysplasia. At 397 nm excitation, the fluorescence increases in the red region of the spectrum for the dysplastic BE sites. Similar changes are observed at 412 nm excitation.

Figure 4:
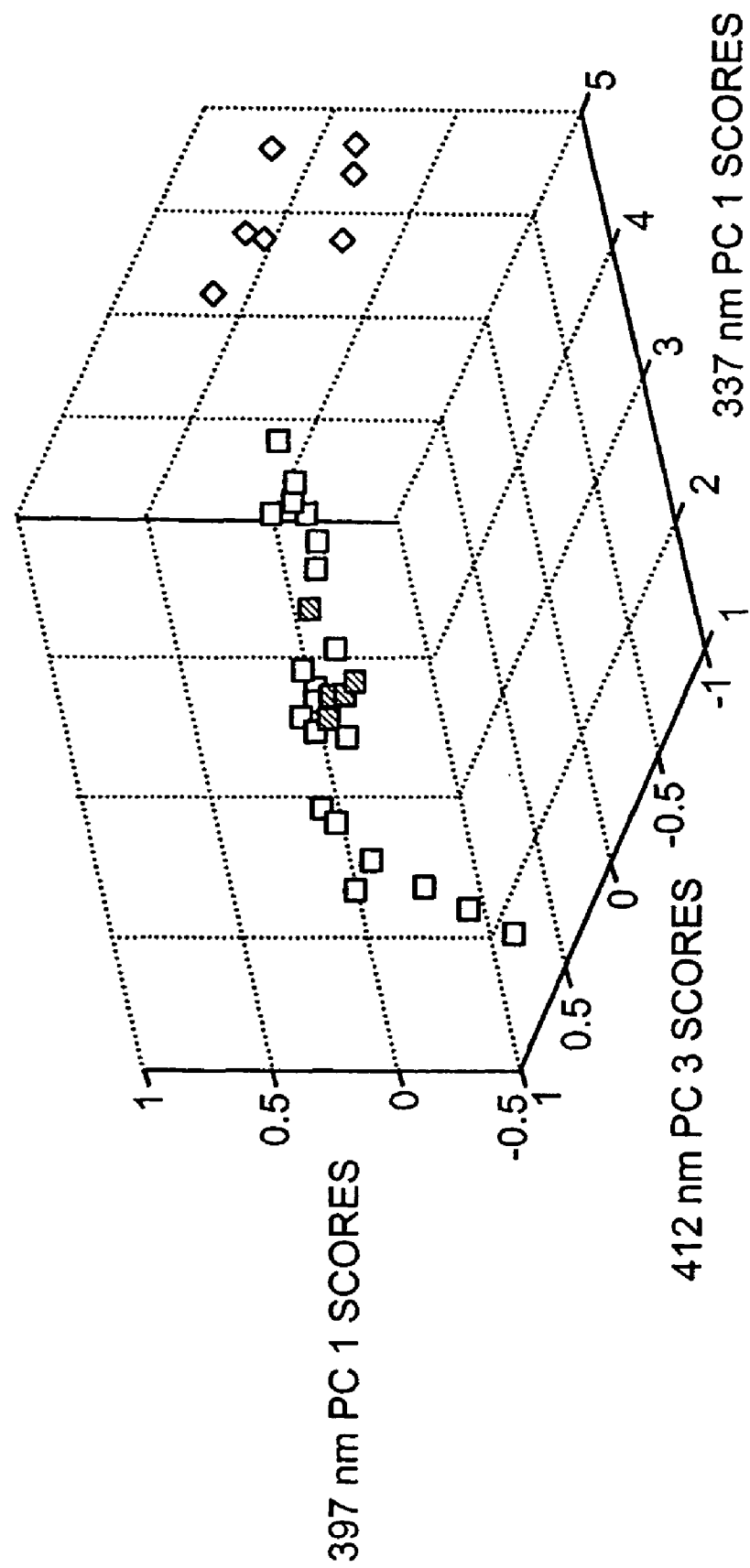
FIG. 4 illustrates the scores of three principal components extracted from the decomposition of intrinsic fluorescence spectra at 337, 397 and 412 nm excitation used to distinguish high-grade dysplasia (diamonds) from non-dysplastic and low-grade dysplasia (squares) Barrett's esophagus (BE) sites. At 337 nm excitation, decomposition was performed in the 460 to 520 nm region of the intrinsic fluorescence spectra, as this is the wavelength range within which spectral differences are most pronounced. Similarly, at 397 nm excitation principal components were extracted from the intrinsic fluorescence spectra between 600 and 650 nm. PC 1 indicates the first principal component and PC 3 the third.
Figure 5:
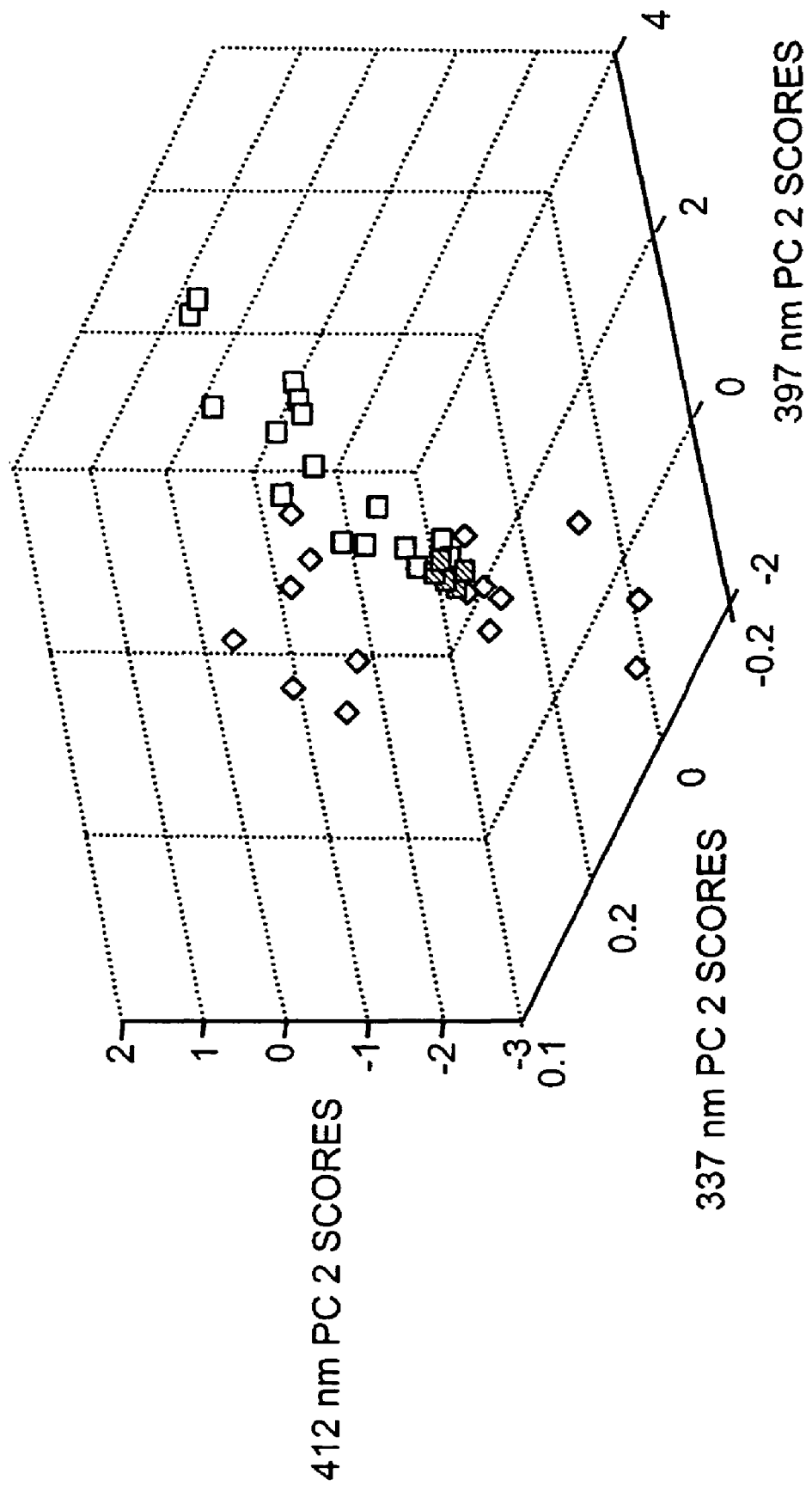
FIG. 5 illustrates the scores of three principal components extracted from the decomposition of the entire intrinsic fluorescence spectra at 337, 397 and 412 nm excitation used to distinguish dysplastic (low- and high-grade; diamonds) from non-dysplastic (squares) Barrett's esophagus (BE) sites. PC 2 indicates the second principal component.

These differences can be used to develop algorithms for detecting dysplasia in BE. Specifically, principal component analysis, logistic regression and leave-one-out cross-validation are employed to determine the sensitivity and specificity with which one can separate (a) non-dysplastic from dysplastic (low- and high-grade) tissue, and (b) high-grade dysplasia from low-grade and non-dysplastic BE epithelium. In each case, the scores of one of the first three principal components extracted from the intrinsic fluorescence spectra at 337, 397, and 412 nm excitation are used (FIGS. 4 and 5). The selected principal components describe the observed spectral differences. From this analysis, sites with high-grade dysplasia can be differentiated from low-grade and non-dysplastic sites with high sensitivity and specificity (Table 1). Additionally, dysplastic and non-dysplastic epithelia can be distinguished with very high sensitivity and specificity.

Table 1 illustrates the accuracy of spectroscopic classification of non-dysplastic (NDB), low-grade (LGD) and high-grade dysplastic (HGD) tissue in Barrett's esophagus.

TABLE 1

| | HGD vs. (LGD and NDB) | | (LGD and HGD) vs NDB | |
|---|---|---|---|---|
| | Sensitivity | Specificity | Sensitivity | Specificity |
| Intrinsic fluorescence (IF) | 100% | 98% | 71% | 92% |
| Reflectance (R) | 86% | 100% | 79% | 88% |

TABLE 1-continued

| | HGD vs. (LGD and NDB) | | (LGD and HGD) vs NDB | |
|---|---|---|---|---|
| | Sensitivity | Specificity | Sensitivity | Specificity |
| Light Scattering (LS) | 100% | 91% | 93% | 96% |
| Combination of IF, R and LS | 100% | 100% | 93% | 100% |

Figure 6:
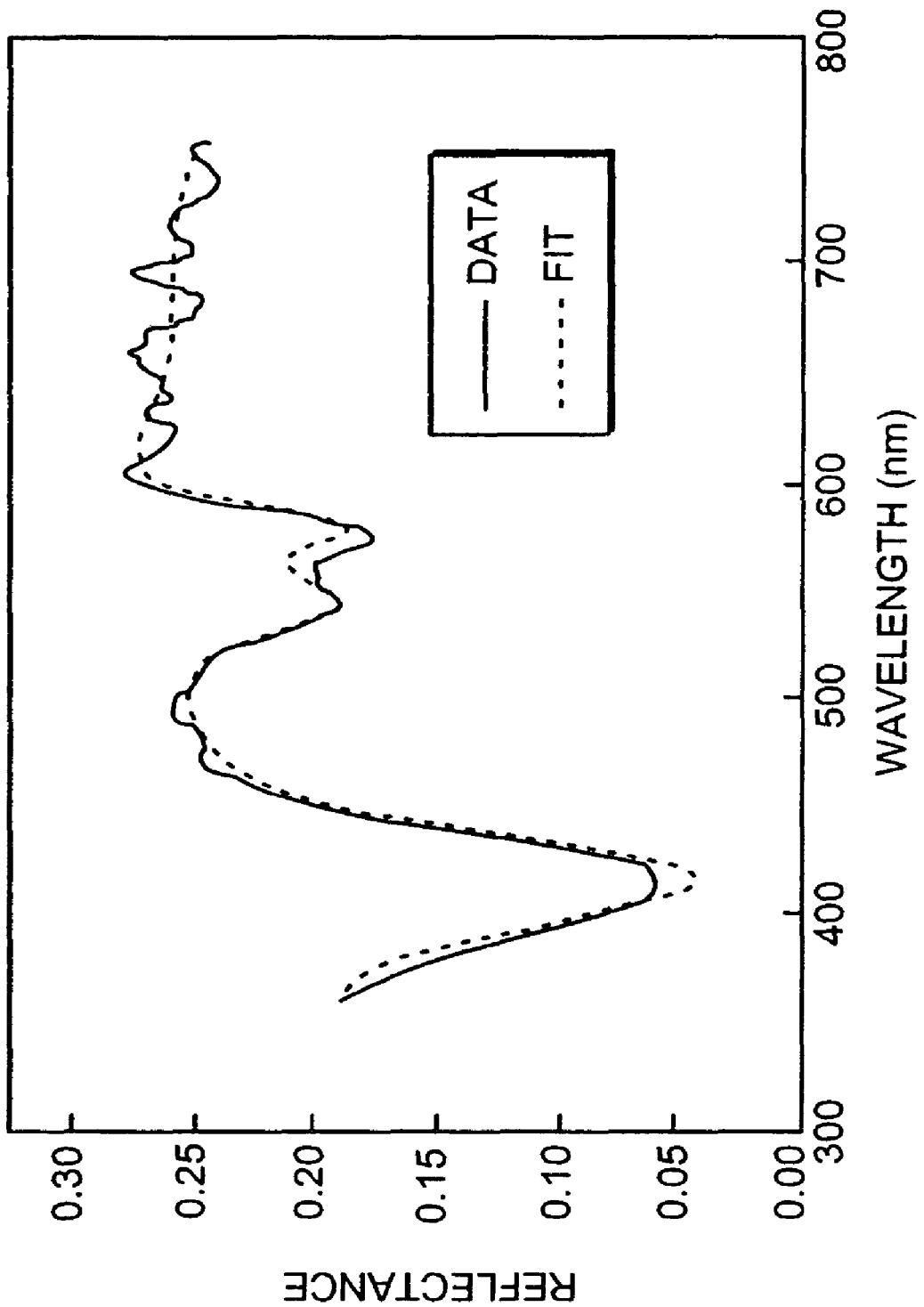
FIG. 6 is a reflectance spectrum of a non-dysplastic Barrett's esophagus site. The solid line represents the measured data and the dashed line represents the projected properties of the tissue based on known scattering and absorption properties of the tissue.

Reflectance spectra can be analyzed using a mathematical representation to obtain detailed information about the scattering and absorption properties of the bulk tissue. A typical reflectance spectrum with the corresponding fit obtained using this representation is shown in FIG. 6.

Figure 7:
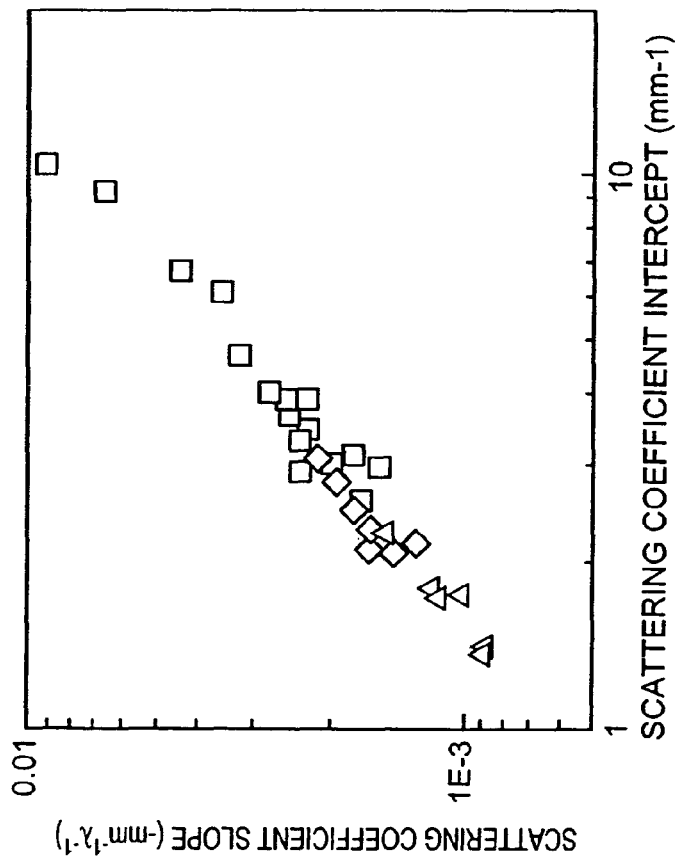
FIG. 7 illustrates graphically the slopes and intercepts of wavelength dependent tissue reduced scattering coefficient, $\mu_s'(\lambda)$, for non-dysplastic (squares), low-grade (diamonds) and high-grade (triangles) dysplastic Barrett's esophagus (BE) sites. In each case, a straight line was fit to $\mu_s'(\lambda)$, extracted from the reflectance spectrum. A log-log scale is used to facilitate visualization of all the data points.
Figure 9C:
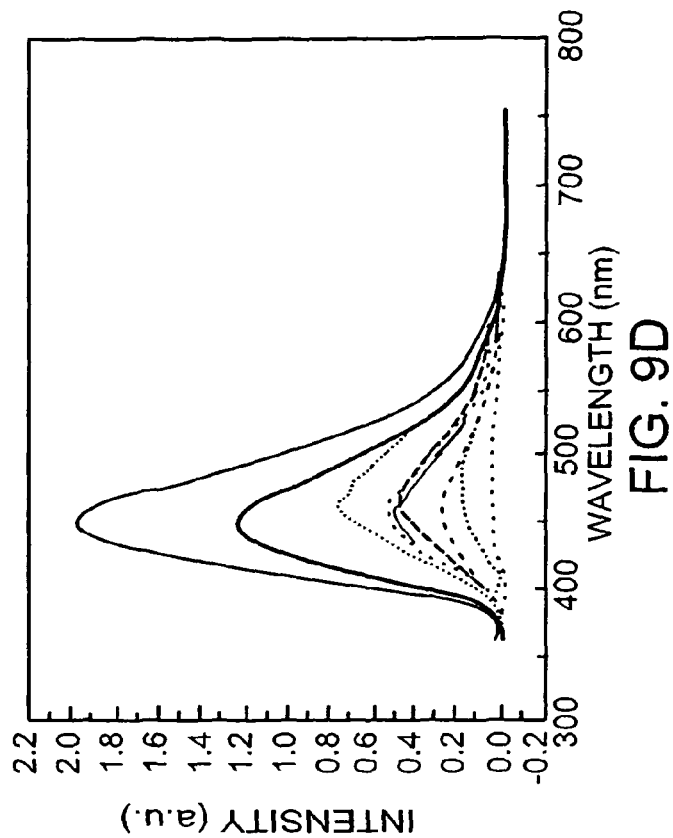
Figure 9D:
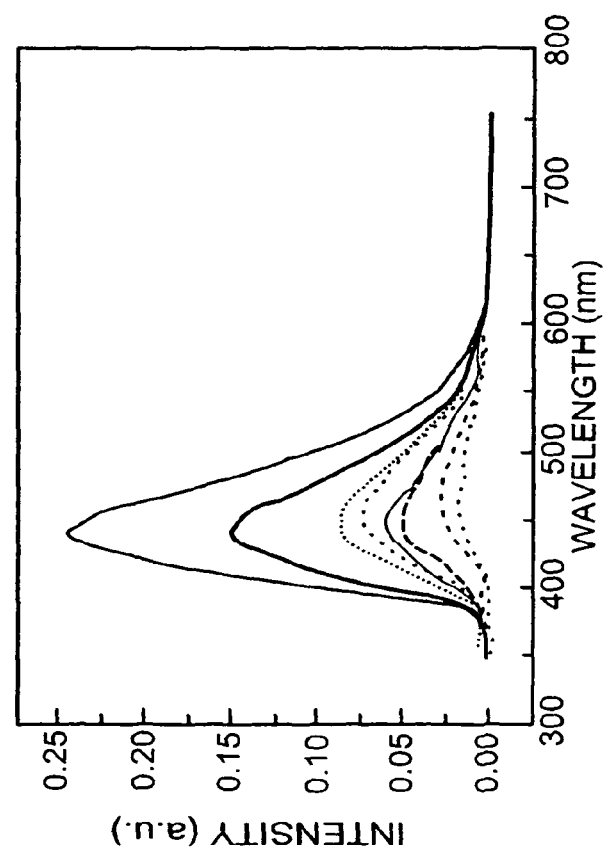

This type of analysis shows that the reduced scattering coefficient $\mu_s'(\lambda)$ of Barrett's esophagus tissue changes gradually during the progression from non-dysplastic, to low-grade, to high-grade dysplasia. For example, at 400 nm the $\mu_s'(\lambda)$ of high-grade dysplastic tissue ($1.3\pm0.2$ mm$^{-1}$) is lower than that of low-grade dysplastic tissue ($1.8\pm0.3$ mm$^{-1}$) which, in turn, is lower than that of non-dysplastic Barrett's esophagus (BE) tissue ($3\pm1.6$ mm$^{-1}$). Additionally, the wavelength dependence of $\mu_s'(\lambda)$ changes during the development of dysplasia. To describe these changes, a straight line is fit to $\mu_s'(\lambda)$ and the intercept and slope of thus line are used as diagnostic parameters (FIG. 7). Using logistic regression and leave-one-out cross-validation, the sensitivity and specificity for classifying tissue in accordance with histopathology are determined. This method results in slightly lower overall sensitivity and specificity values than those achieved with the intrinsic fluorescence spectra (Table 1).

Figure 8:
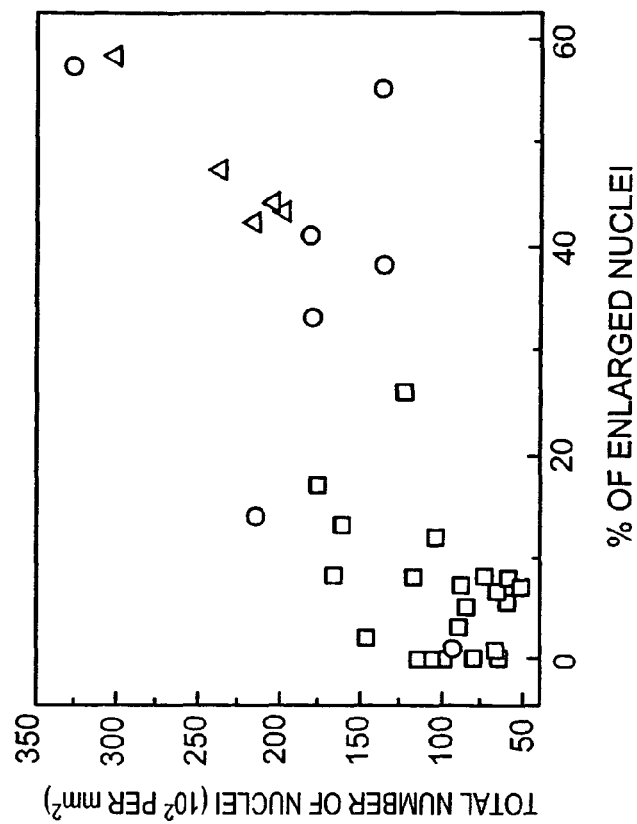
FIG. 8 illustrates the total number of nuclei per mm$^2$ plotted as a function of percentage of enlarged nuclei (diameter>10 µm), as determined from the light-scattering model analysis. Non-dysplastic Barrett's are represented by squares, low-grade dysplasia are represented by circles; and high-grade dysplasia are represented by triangles.

The reflectance spectra are further processed in a manner that allows extraction and analysis of the backscattered light from the epithelial cell nuclei. The results of this analysis are displayed in FIG. 8. The ordinate of FIG. 8 represents the number of nuclei per square mm, indicative of the degree of nuclear crowding, and the abscissa represents the percentage of enlarged nuclei, defined as nuclei having diameter greater than 10 microns. Note that the non-dysplastic samples are concentrated in the lower left-hand corner, indicating cell nuclei that are small and free of crowding. As dysplasia progresses, the data points move to the upper right, indicating nuclear enlargement and crowding, in agreement with the findings of histopathology. This technique is superior in terms of separating the dysplastic (low- and high-grade) from the non-dysplastic BE sites (Table 1).

The ability to characterize dysplastic and non-dysplastic tissue in BE is improved by combining the information provided by each one of the spectroscopic techniques, obtained simultaneously with our system. When a spectroscopic classification is consistent with at least two of the three analysis methods, high-grade dysplasia is identified with perfect sensitivity and specificity, and dysplastic tissue is distinguished from non-dysplastic tissue with perfect specificity, while maintaining very high sensitivity (Table 1).

Spectroscopic techniques use information contained in light signals to assess the state of biological tissue. Optical fiber technology allows spectroscopic methods to be applied as a diagnostic tool for a wide range of tissues that are accessible endoscopically. The use of spectroscopy as described herein can be used for improving the physician's ability to detect pre-cancerous (dysplastic) and early cancerous lesions in many organs, such as the oral cavity, the cervix, the lung, the breast and the gastrointestinal tract. Depending on the technique employed, specific information can be acquired about tissue biochemical, architectural and morphological features. Microscopic changes in these features that occur during the progression of dysplasia may be detectable spectroscopically before the manifestation of macroscopic changes that are visible endoscopically. Additionally, spectroscopic techniques are non-invasive, allowing study of the tissue in its native state, free of artifacts introduced by cutting and chemically processing the tissue. In principle, spectroscopic signals can be analyzed in real-time, thus guiding the physician to biopsy areas that are likely to yield significant pathology or possibly allowing her to make an immediate decision on the type of intervention that is required for successful treatment of the patient. Furthermore, the spectroscopic signals carried by light can be used as objective guides for assessing a particular tissue site, especially in areas in which the intra- and inter-observer agreement on the classification of disease is not very good.

The targets of fluorescence spectroscopy include tissue biochemicals such as NADH, FAD, collagen, elastin and porphyrins. Exogenous or exogenously-induced chromophores that have been shown to accumulate preferentially in the diseased areas can also be used. The detection of high-grade dysplasia using tissue autofluorescence excited at 410 nm have been conducted. The difference between the measured integrated intensity-normalized fluorescence and the mean normalized fluorescence from normal esophageal tissue was used for the diagnostic procedure. The main spectral features that resulted in good differentiation between high-grade dysplastic and non-dysplastic tissues were the presence of decreased fluorescence around 470-480 nm and increased fluorescence in the red region of the spectrum for the high-grade dysplastic tissues. However, this process does not classify correctly sites with low-grade or focal high-grade dysplasia.

In the present example illustrating an embodiment of the invention fluorescence spectra at 11 different excitation wavelengths between 337 and 610 nm were obtained. Thus, instead of a single fluorescence spectrum an excitation-emission matrix (EEM) is collected. EEMs can be used to identify the excitation wavelengths at which tissue classification is optimized. Additionally, EEMs can assist in identifying the origins of the measured fluorescence signals in a more reliable manner. Nevertheless, as shown in FIGS. 2 and 3, these measured EEMs can be distorted significantly by tissue scattering and absorption. To eliminate artifacts introduced by changes in scattering or absorption, rather than by tissue biochemistry, corresponding reflectance spectra can be used which are affected in a similar manner by scattering and absorption events. Once the distorted measured tissue fluorescence spectra are rectified using the reflectance, tissue fluorescence excited at 337 nm broadens and shifts to longer wavelengths in a very consistent manner as the tissue progresses from non-dysplastic to low-grade to high-grade dysplasia (FIG. 3). These spectral changes are consistent with the presence of increased NADH levels in dysplastic tissue. Our findings at 397 and 412 nm excitation are attributed to endogenous porphyrins. The spectra corresponding to the high-grade dysplasia sites appear slightly distorted around 470 nm, even after correcting for the effects of scattering and absorption. This suggests that this difference arises as a result of biochemical changes rather than absorption changes.

To demonstrate the level of significant changes that are observed in tissue fluorescence during the development of dysplasia, the scores of one of the first three principal components which described over 99% of the variance observed in the intrinsic fluorescence spectra excited at 337, 397 and 412 nm can be used. Subsequently, one can use logistic regression and leave-one-out cross-validation to estimate and validate in an unbiased manner the sensitivity and specificity with which one can distinguish (a) high-grade dysplasia from low-grade and non-dysplastic tissue, and (b) dysplastic (low- and high-grade) from non-dysplastic tissue to separate high-grade dysplasia from low-grade and non-dysplastic tissue, spectroscopic classification is consistent with histopathology in all but one case. Additionally, one can distinguish dysplastic from non-dysplastic tissue with very high sensitivity and specificity.

Reflectance spectroscopy can be used not only to remove the distortions observed in the measured tissue fluorescence spectra, but also to provide very detailed and potentially useful information about morphological and architectural features of the tissue. Specifically, as shown in FIG. 6 the observed tissue reflectance spectra can be used in terms of two parameters that are determined by tissue scattering and absorption. For example, changes in the concentration or the oxygen saturation of hemoglobin, the main absorber in the visible spectrum for this tissue type, result in concomitant changes in the absorption coefficient of tissue. Alterations in the architecture of the connective tissue collagen fibers, one of the main contributors of tissue scattering, lead to a modified tissue scattering coefficient. The analysis suggests that the scattering coefficient of tissue decreases significantly during the development of dysplasia, suggesting that changes that are not observed histopathologically are taking place within the lamina propria and submucosa before the onset of invasion. Recently, it has been shown that an increased level of cysteine and serine proteases is found in gastric and colorectal cancerous and precancerous lesions. The findings related to the decrease in the value of the scattering coefficient during the progression of dysplasia are consistent with the presence of such enzymes, which can result in a less dense collagen matrix, for instance. The change in the slope of $\mu_s'(\lambda)$ as a function of wavelength suggests that the mean size of the tissue scattering particles is changing. Crowding of the cells and nuclei of the epithelial layer may be responsible for this change. As shown in Table 1, one can use the observed changes in tissue scattering to classify tissue quite successfully. Light scattering spectroscopy is a procedure that can be used to obtain information about the number and the size of nuclei of the epithelial cell layer. Epithelial cell nuclei are the primary targets of reflected light that is singly scattered before it is collected by a probe. The intensity and oscillations of this singly-backscattered light are characteristic of the number and size of its target nuclei. This technique is used to characterize pre-cancerous and early cancerous changes in the colon, the oral cavity, the bladder and Barrett's esophagus (BE). Results of this technique are included for the data set of a preferred embodiment to illustrate the information that can be acquired and combined with fluorescence and reflectance spectroscopies. Light scattering spectroscopy outperforms the other two methods in terms of its ability to separate the dysplastic from non-dysplastic BE sites.

The combination of all three techniques provides an extremely sensitive and specific tool for the detection of dysplasia in Barrett's esophagus (BE). In this case, agreement with histopathology is achieved in terms of separating high-grade dysplasia from non-dysplastic and low-grade dysplasia sites. Additionally, all sites are classified correctly as dysplastic or non-dysplastic, with the exception of one site. The observed improvement is expected, since each one of the techniques examines different features of tissue biochemistry and morphology that can be altered during the development of dysplastic changes.

Pancreatic carcinoma is one of the first five leading causes of death in Western countries and has a very poor prognosis after initial diagnosis. This is due to late presentation of symptoms and the fact that only about 5-20% of all patients are eligible for resection. Adenocarcinoma of the pancreas arises from the ductal epithelium. In the precancerous stages ductal epithelial cells undergo morphological changes similar to those of Barrett's esophagus (BE) including increasing nuclear size and crowding. Several clinical conditions exist which may allow detection of precancerous or early cancerous changes. These include acute or chronic pancreatitis due to focal obstruction of the pancreatic duct, acute pancreatitis due to intraductal papillary mucinous tumor of the pancreas (IPMT), and patients with a strong family history of pancreatic cancer. Detection of dysplasia in this setting is currently based on the detection of stricturing or dilation of the pancreatic duct, and exfoliative cytology. However, these methods cannot reliably distinguish dysplasia and inflammation and have an overall poor sensitivity of 44-70%.

The present invention includes methods for performing tri-modal spectroscopic analysis within the main pancreatic duct using the technique of endoscopic retrograde cholangiopancreatography (ERCP), and obtained spectra from the pancreatic duct epithelium.

The majority of patients with ductal adenocarcinoma of the pancreas present with late stage tumors that are not amenable to curative therapy. A significant minority of patients present for evaluation at a time where early dysplasia of carcinomas are detectable. These include strictures of the main pancreatic duct (MPD), and IPMT presenting as acute pancreatitis, and in patients with a strong family history of carcinoma of the pancreas. In all of these cases, the presence of dysplasia, and the distribution of dysplasia along the length of the pancreas are critical to management decisions (whether to remove part of all of the pancreas). The present invention can be directed to the use of tri-modal spectroscopy for the detection of dysplasia an invasive cancer in the pancreatic duct. The present invention can evaluate ex vivo or in vivo specimens of patients to detect pancreatic cancer of dysplasia. Spectra can be collected from the MPD at 1 cm intervals within 3 hours of resection and before formalin fixation. Tri-modal spectral analysis can be performed to evaluate for components which accurately discriminate histological categories. These spectral algorithms can be applied in vivo to patients undergoing endoscopic retrograde cholangiopancreatography for evaluation of the 3 conditions mentioned above. Spectra can be collected in vivo at 1 cm intervals along with entire length of the duct. Spectral signals can be compared to histology among the patients whose clinical condition dictates surgical removal of the pancreas. Anatomic locations of the spectral signals can be matched according to the distance from MPD orifice.

The present invention can be employed for the detection of pre-invasive disease of the cervix either alone or at the time of colposcopy following an abnormal Pap smear. The present invention can also be used for a non-invasive method of monitoring the progress of medical therapies for pre-invasive disease.

The Pap smear is a screening tool for cervical tissue abnormalities. Abnormal Pap smears are routinely followed up by colposcopy. This process uses a low-power binocular microscope for the identification of abnormal cervical epithelium, which is subsequently biopsied and examined histopathologically. It is estimated that in expert hands the sensitivity and specificity of colposcopy are 94% and 48%, respectively.

A preferred embodiment of the present invention include spectroscopic techniques to evaluate cervical epithelium in vivo. Tissue fluorescence spectra excited at 337, 380 and 460 nm were acquired during colposcopy from normal and suspicious sites within the ectocervical and endocervical regions. Suspicious sites were biopsied and classified histopathologically. An initial set of spectra was analyzed and statistical methods were developed to optimize the agreement between spectroscopic and histopathological classification. When these methods were used prospectively to classify a second set of data, it was found that squamous intraepithelial lesions (SILs) can be identified spectroscopically with 82% sensitivity and 68% specificity when compared to histopathology. The present invention improves upon the sensitivity and specificity of spectral analysis of cervical epithelium in a real-time in vivo approach. The method employs tri-modal spectroscopy (TMS), the combined use of intrinsic fluorescence spectroscopy (IFS), diffuse reflectance spectroscopy (DRS), and light scattering spectroscopy (LSS).

The method can compare the spectra obtained using tri-modal processing with the histologic diagnosis of the area of epithelium biopsied. This process provides patterns that are predictive of histologic dysplasia in a prospective fashion, thus allowing the clinician to increase the positive histologic lesions of the cervical epithelium prospectively. This can be of immense value in following patients on clinical trials in order to determine the response to medical treatments of cervical dysplasia.

Spectra can be acquired from the normal squamous ectocervix and suspicious sites within the transformation zone. The latter may be biopsied immediately following spectral acquisition. Data has been collected from 34 patients, 42 normal ectocervical sites (not biopsied), 15 benign biopsied sites (12 classified as squamous metaplasia and 3 as mature squamous epithelium) and 10 high-grade squamous intraepithelial lesions (HSILs).

Differences in the intrinsic fluorescence intensity and/or lineshape are observed for several excitation wavelengths as shown in FIGS. 9A-9D.

Instead of using principal component analysis for the assessment of the diagnostic potential of intrinsic fluorescence spectroscopy, the spectra may be decomposed as a linear combination of the NADH and collagen EEMs extracted from the measurements performed during variceal ligation.

Figure 10:
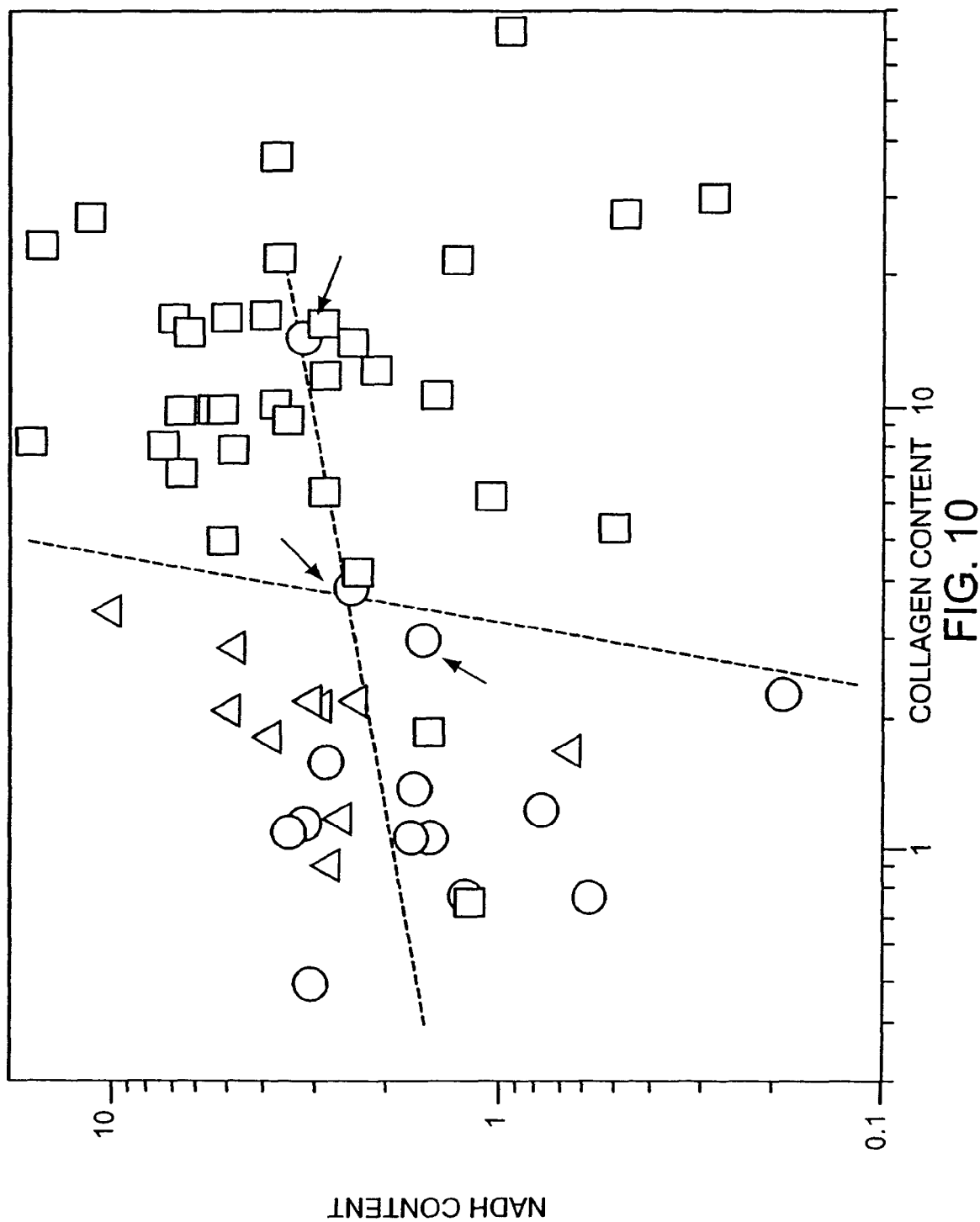
FIG. 10 illustrates relative NADH fluorescence levels as a function of relative collagen fluorescence levels plotted for normal squamous epithelium (squares), benign biopsies (circles) and HSILs (triangles). The three arrows point to the benign biopsies that were classified as "mature squamous epithelium." The remaining benign biopsies were classified as "squamous metaplasia."

A significant decrease is observed in collagen fluorescence of the benign biopsied sites and HSILs compared to that of the normal squamous epithelium as seen in FIG. 10. These changes result from differences in the levels of expression of matrix metalloproteinases (MMPs), a class of enzymes responsible for collagen degradation. Differences in the levels and/or patterns of expression of MMP-2 have been reported between normal squamous epithelium, squamous metaplasia and SILs. Additionally, an increase in the NADH fluorescence is noted for the HSILs compared to that of benign biopsied sites as seen in FIG. 11A. This increase can be the result of an increase in the number of epithelial cells and/or their metabolic activity (52). Using logistic regression and "leave-one-out" cross-validation, as in the case of Barrett's esophagus, HSILs can be distinguished from the benign biopsied sites with a sensitivity of 80% and a specificity of 67%.

Analysis of the diffuse reflectance spectra using the periodic component in the scattered light indicates that the reduced scattering coefficient of the HSILs is generally lower than that of the squamous metaplastic and mature squamous epithelium biopsied sites as seen in FIG. 11B. When the value of $\mu_s'(\lambda)$ at 400 nm is used to perform logistic regression and cross-validation, 7/10 HSILs (70% sensitivity) and 9/15 benign biopsied sites (60% specificity) are classified correctly.

Extraction and analysis of the light scattering spectra indicated that the variation in nuclear size, i.e. the standard deviation of the nuclear size population corresponding to a particular site, has a higher diagnostic value than the percentage of enlarged nuclei considered in the case of Barrett's esophagus. Using logistic regression and cross validation with the nuclear size standard deviation and the number of nuclei per unit area as diagnostic parameters, HSILs may be separated from the benign biopsied sites with 90% sensitivity and 67% specificity as seen in FIG. 11B.

Finally, the three techniques, IFS, DRS and LSS, are combined in a preferred embodiment in a manner that classifies a particular site according to the diagnosis that is consistent with at least two of the three methods of analysis. This approach leads to a high level of sensitivity and specificity (100% and 80%, respectively) for the detection of HSILs from non-HSIL sites biopsied within the transformation zone when compared to any one of the techniques alone as seen in Table 2.

TABLE 2

|  | benign biopsies vs HSIL | |
| --- | --- | --- |
|  | Sensitivity | Specificity |
| Intrinsic Fluorescence Spectroscopy (IFS) | 80% | 67% |
| Diffuse Reflectance Spectroscopy (DRS) | 70% | 60% |
| Light Scattering Spectroscopy (LSS) | 90% | 67% |
| Tri-Modal Spectroscopy (TMS) | 100% | 80% |

Figure 12:
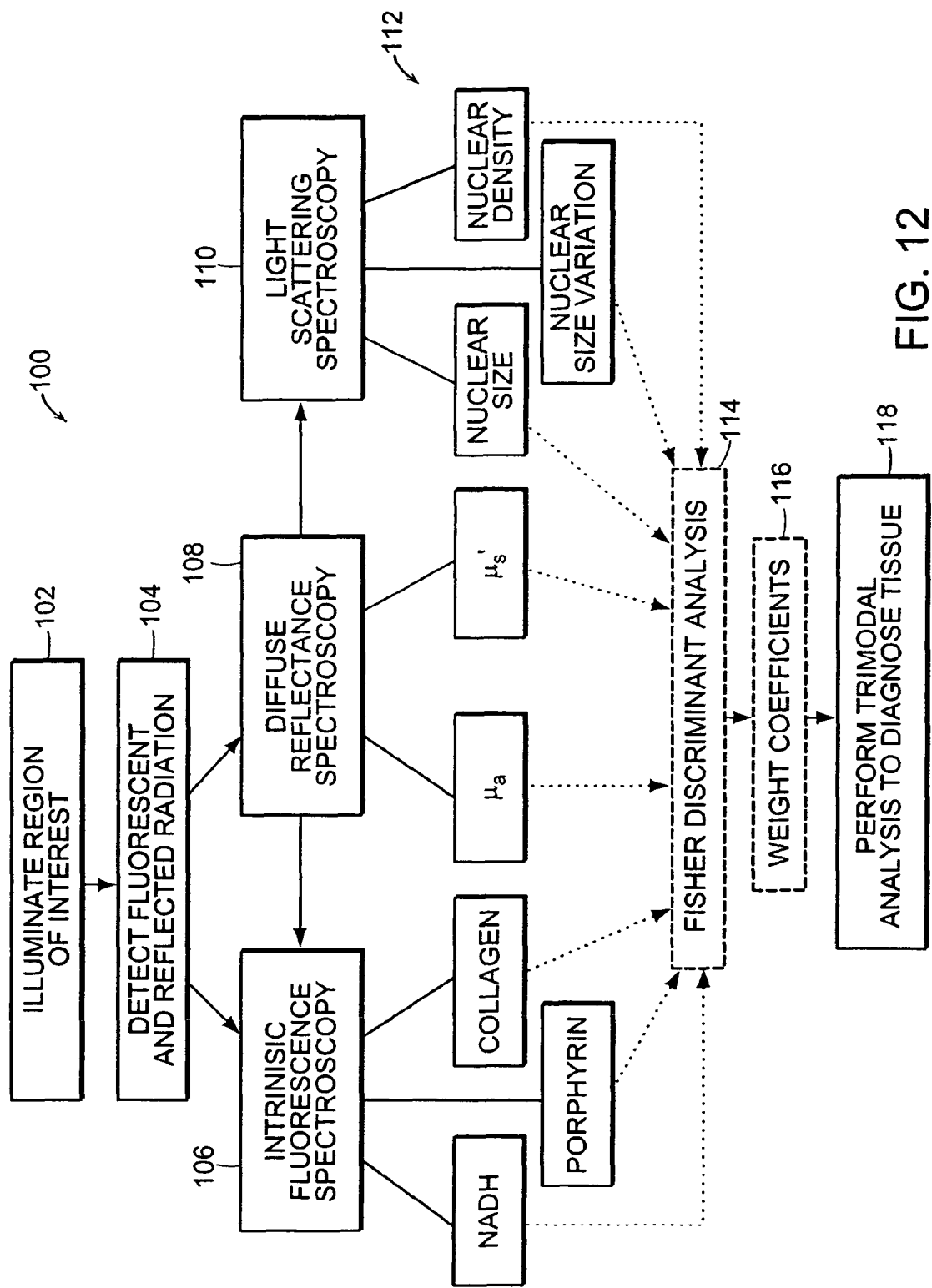
FIG. 12 illustrates a process sequence in accordance with a preferred embodiment of the present invention.

FIG. 12 illustrates a process sequence 100 of a preferred embodiment of the invention in which a region of interest within a lumen of a patient is illuminated 102 and the fluorescent and reflected light is detected 104. The three components 106, 108 and 110 are used to generate structural and biochemical information 112. This data can be analyzed using discriminant analysis 114, the components weighted 116, and a diagnosis performed 118 in real-time. These measurements demonstrate the ability of spectroscopic techniques to provide useful information for disease classification in a non-invasive manner. While each of the techniques can be used for detecting dysplasia in Barrett's esophagus, their combination allows the formation of a comprehensive picture of the biochemical and morphological state of tissue. Specifically, decomposition of the intrinsic tissue fluorescence EEMs into EEMs of biochemicals such as NADH and collagen can provide details about tissue biochemistry. Reflectance and light scattering spectroscopy yield morphological information related to the connective tissue and the epithelial cell nuclei. As this information is free from artifacts introduced by tissue excision and processing, it can help advance the understanding of the processes that lead to the progression of dysplasia. Software for performing data analysis in real-time enables the applicability of these techniques as a guide to biopsy. Methods to image regions of interest using this procedure enables large tissue areas to be studied rapidly.

An operating environment for the system includes a processing system such as data processing system 34, with at least one high speed processing unit and a memory system. In accordance with the practices of persons skilled in the art of computer programming, the present invention is described with reference to acts and symbolic representations of operations or instructions that are performed by the processing system, unless indicated otherwise. Such acts and operations or instructions are sometimes referred to as being "computer-executed," or "processing unit executed."

It will be appreciated that the acts and symbolically represented operations or instructions include the manipulation of electrical signals by the processing unit. An electrical system with data bits causes a resulting transformation or reduction of the electrical signal representation, and the maintenance of data bits at memory locations in the memory system to thereby reconfigure or otherwise alter the processing unit's operation, as well as other processing of signals. The memory locations were data bits are maintained are physical locations that have particular electrical, magnetic, optical, or organic properties corresponding to the data bits.

The data bits may also be maintained on a computer readable medium including magnetic disks, optical disks, organic disks, and any other volatile or non-volatile mass storage system readable by the processing using. The computer readable medium includes cooperating or interconnected computer readable media, which exist exclusively on the processing system or is distributed among multiple interconnected processing systems that may be local or remote to the processing system.

Figure 13:
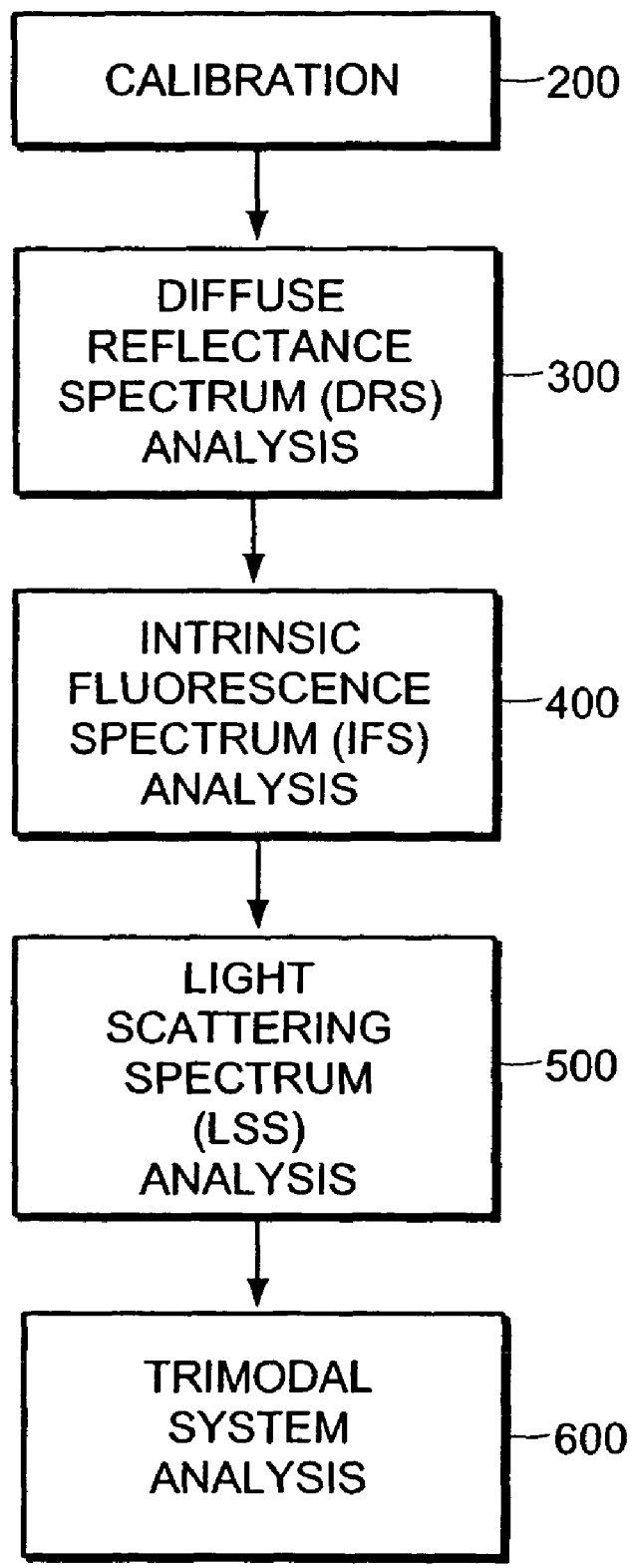
FIG. 13 illustrates a flow chart of a preferred embodiment for measuring a structure in a layer of tissue in accordance with the present invention.

FIG. 13 is a flowchart of a preferred embodiment of measuring a structure in a layer of tissue by analyzing data in real-time in accordance with the present invention. The real-time analysis may be used to diagnose a pre-cancerous condition in, for example, epithelial tissue in the cervix and GI tract. The measurement process begins with the step 200 of calibration. The diffuse reflectance spectrum (DRS) is then analyzed per step 300. In step 400 the intrinsic fluorescence spectrum (IFS) is analyzed. The next step in the process includes the step 500 of analyzing the light scattering spectrum (LSS). The method then proceeds to step 600, which represents the combined analysis for the previous modes of this tri-modal system analysis.

In a preferred embodiment, during an endoscopic procedure, fluorescence spectra at a plurality of wavelengths, for example, at eleven laser excitation wavelengths between 337 and 620 nm and one white light (350-750 nm) reflectance spectrum is acquired in less than one second. Light delivery and collection is mediated through an optical fiber probe. The acquired spectra contain information about the uppermost tissue layers, where almost 90% of cancers begin.

From the recorded fluorescence and reflectance spectra, three types of spectroscopic information is extracted: IFS, DRS and LSS. The IFS refers to the recovery of tissue fluorescence spectra that are free of distortions introduced by tissue scattering and absorption. To remove these distortions, the measured fluorescence and reflectance spectra are combined using, for example, a photon-migration-based method. The extracted IFS is decomposed to provide quantitative information on the biochemical tissue composition and the changes that take place in pre-cancerous tissues.

The measured reflectance spectra consists mainly of photons that are scattered many times before being detected. A model that is based on diffusion theory is used to describe the diffusely reflected light and thus to extract information about the absorption and the reduced scattering coefficients of tissue. The reduced scattering coefficient depends mainly on the morphology of connective tissue, which provides structural support for the epithelium, the most superficial tissue layer.

The combined use of the IFS, DRS and LSS serves as a tool for biophysical tissue characterization and detection of pre-cancerous lesions. In a preferred embodiment, the TMS analysis may be performed in 2-8 seconds from time of data collection. This TMS analysis can provide a real-time guide to biopsies.

Figure 14:
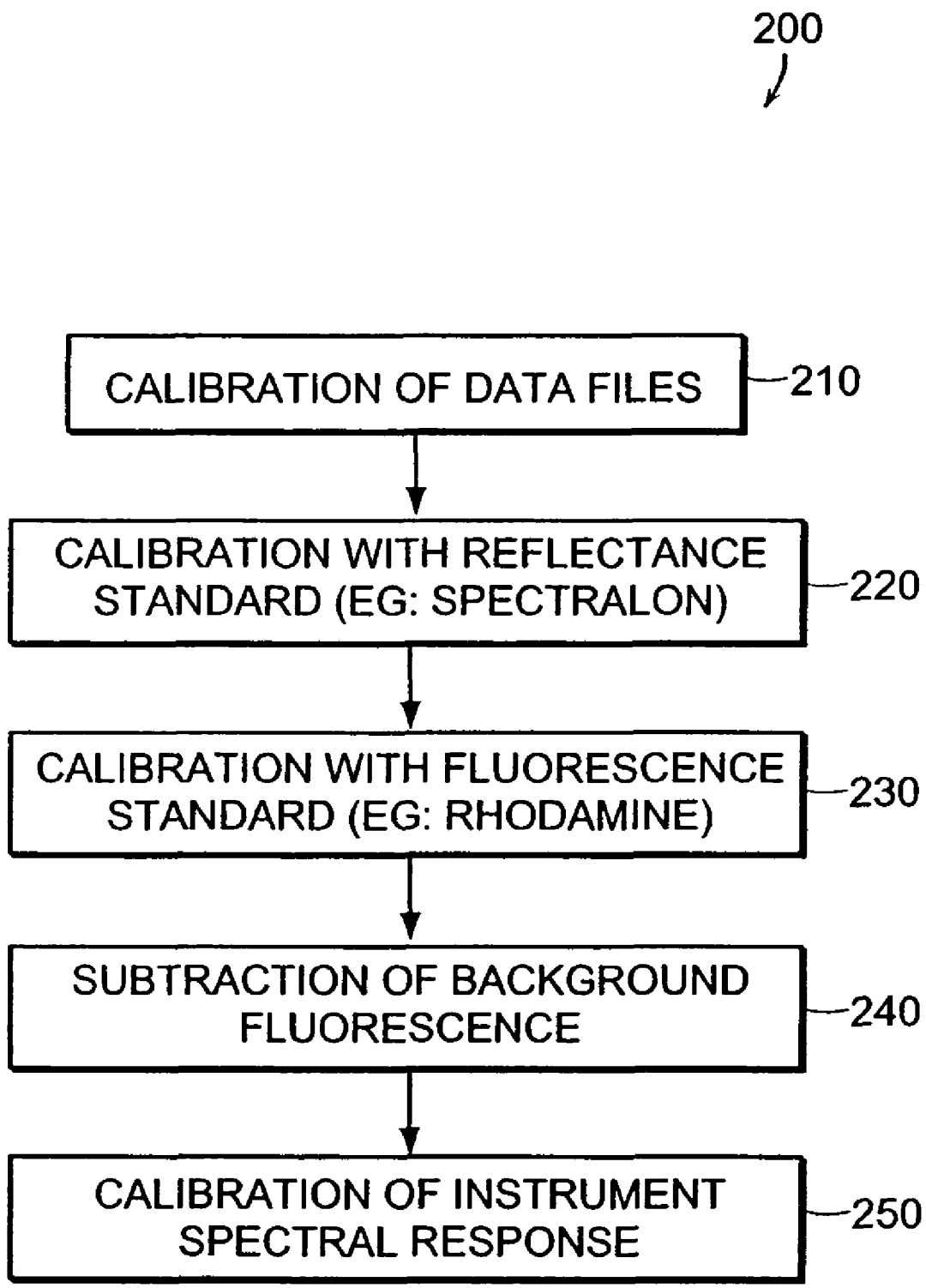
FIG. 14 illustrates the details of the step of calibration referred to in FIG. 13 in accordance with a preferred embodiment of the present invention.

FIG. 14 illustrates the details of the step 200 of calibration in accordance with a preferred embodiment of the present invention. The process of calibration to remove variations in spectra associated with, for example, instruments begins with step 210 of calibrating any data files in the system that are used to diagnose diseased tissue. The next step in the calibration sequence includes the step 220 of calibrating the system with a reflectance standard. This standard may include but is not limited to, for example, the use of a white light standard such as Spectralon calibration of reflectance. The calibration method 200 includes the step 230 of calibrating the system with a fluorescence standard. The fluorescence standard may be, for example, and without limitation, Rhodamine. The next step in the calibration method 200 includes the step 240 of removing the background fluorescence such as, for example, by subtracting any background fluorescence. The spectral response of the instrument is calibrated per step 250.

Figure 15:
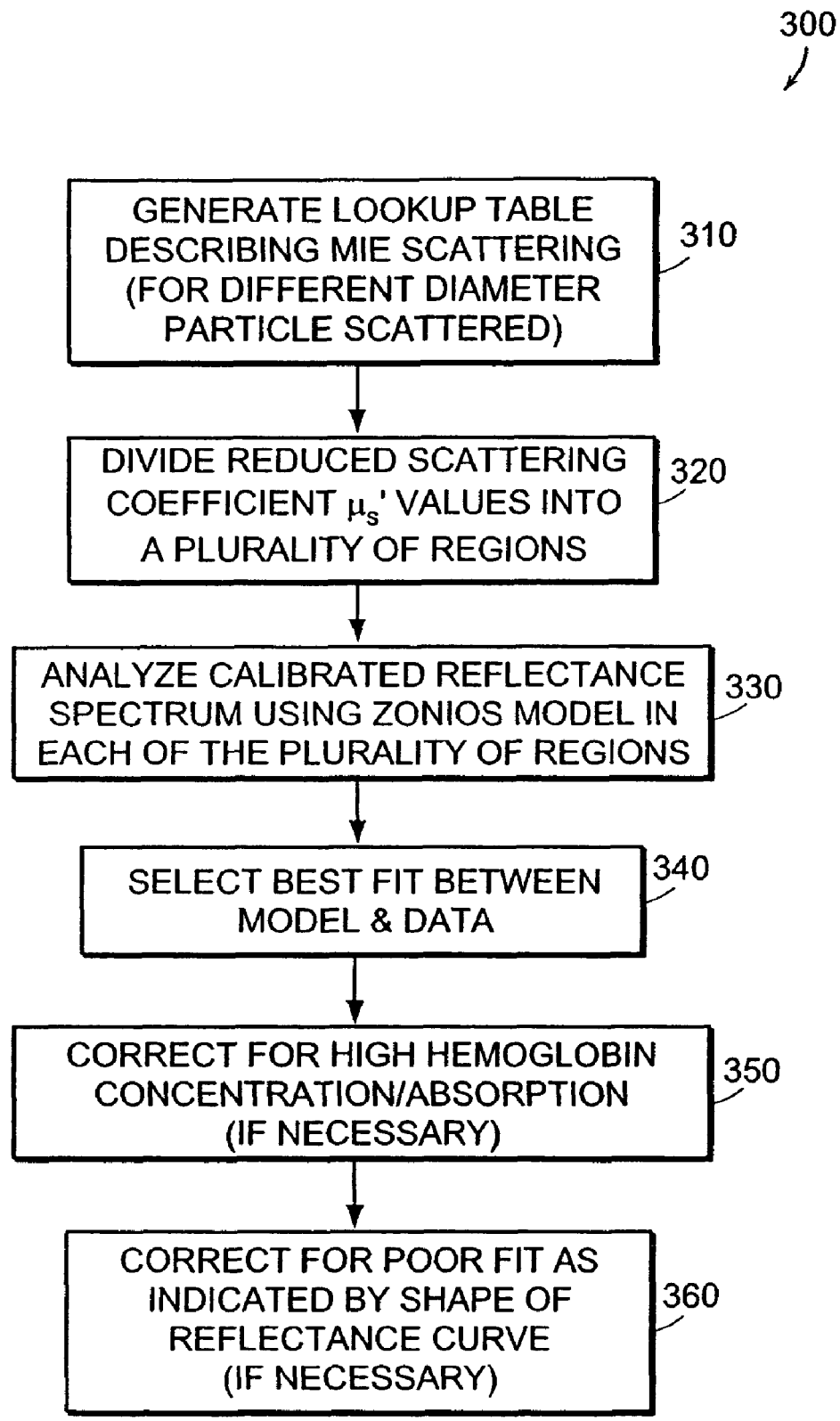
FIG. 15 is a flow chart of a preferred embodiment of the present invention detailing the analysis of the diffuse reflectance spectrum (DRS) in accordance with the present invention.

FIG. 15 is a flow chart of a preferred embodiment of the present invention detailing the analysis of the DRS. The process includes the generation of a look-up table which describes the Mie scattering parameter for different diameters of scattered particles per step 310. The creation of the look-up table describing Mie scattering reduces processing time for Mie scattering calculations for each iteration. Step 320 includes dividing the reduced scattering coefficient values $\mu_s'(\lambda)$ into a plurality of different regions. In a preferred embodiment, there are five regions. This division into different regions accounts for the lack of one optimum or universal fit for all $\mu_s'(\lambda)$ values, as there are different values for $\mu_s'(\lambda)$ in different regions. Thus, the $\mu_s'(\lambda)$ space is separated into a plurality of regions and a minimization process is performed for each region separately. In step 330, the calibrated reflectance spectrum is analyzed using a model, for example, the model described in previously referenced U.S. Pat. No. 6,091,984 and referenced herein after as the Zonios model in each of the different regions. The Zonios model accounts for one layer tissue architecture and represents an iterative process to get a best fit between the results of the model and values from an actual recording. A preferred embodiment of the present invention includes accounting for a multi-layer tissue architecture such as a two-layer model. In the Zonios model light is provided onto a surface of a tissue by a light source. The light reflected back from the tissue is a function of wavelength and depends on several parameters such as the absorption coefficient of tissue, the reduced scattering coefficient and the probe. Thus, the reflectance spectrum $R(\lambda)=F(\mu_\alpha(\lambda), \mu_s'(\lambda), r_c)$ wherein $\mu_\alpha(\lambda)$ is the absorption coefficient of tissue indicative of hemoglobin or betacarotine or more generally a biochemical that absorbs light, $\mu_s'(\lambda)$ is the reduced scattering coefficient and $r_c$ is the effective light collection area of the probe. A best fit is then selected between the model and data per step 340. The best fit is determined by optimizing values of parameters, for example, a scaling constant, particle size and density and hemoglobin concentration and saturation within a predetermined space. In step 350 a correction is calculated and applied for high hemoglobin concentrations and/or absorption if necessary. Typically the fit is not good when the concentration of hemoglobin is high. In a preferred embodiment if the hemoglobin concentration fit exceeds a predetermined threshold value, the fit is only performed for a region, for example, 450-700 nm. Further, a correction may also be calculated and applied for a poor fit as indicated by the shape of the reflectance curve if necessary per step 360.

Figure 16:
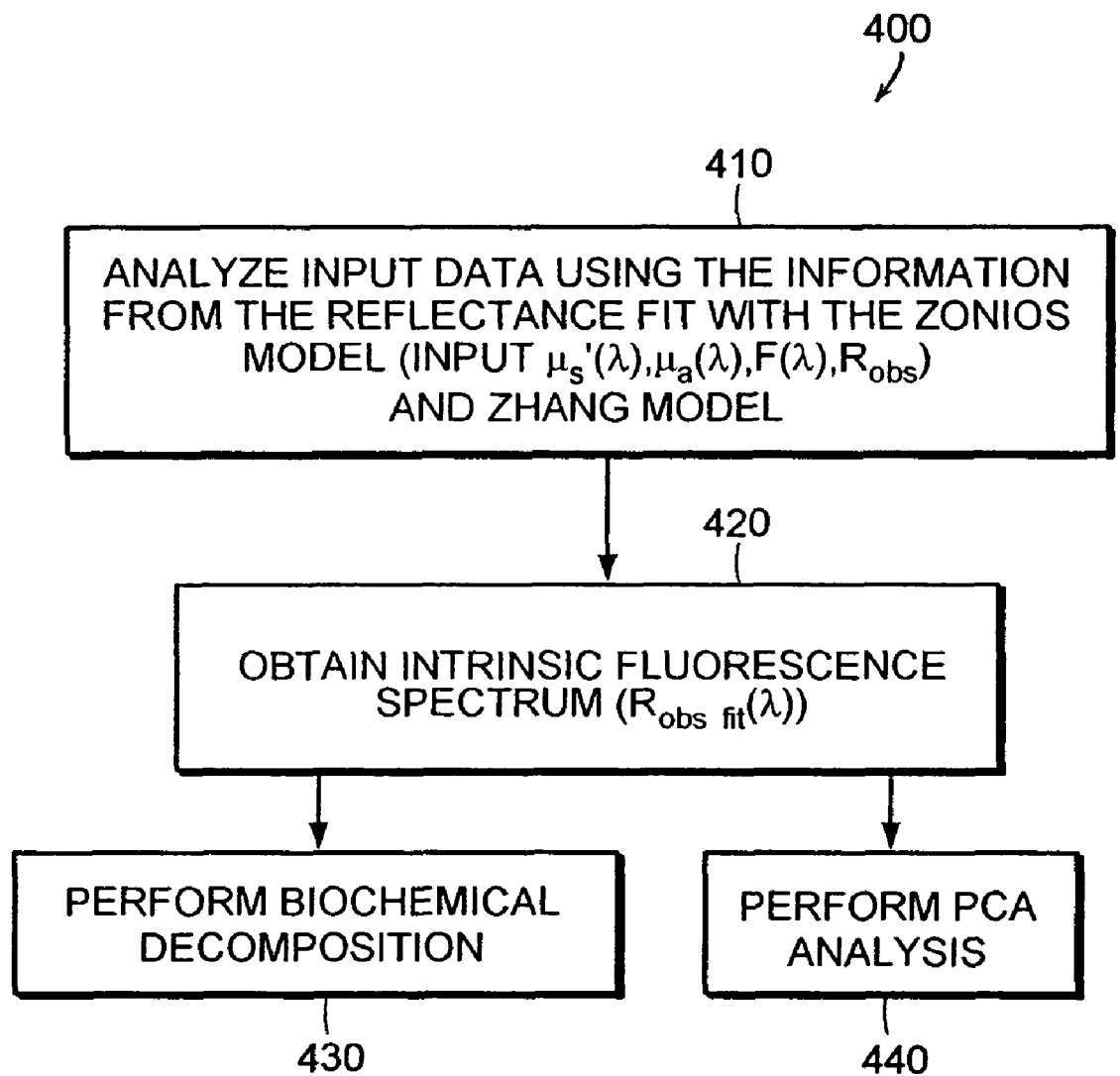
FIG. 16 is a flow chart detailing the analysis of the intrinsic fluorescence spectrum (IFS) in accordance with a preferred embodiment of the present invention.

FIG. 16 is a flow chart detailing the analysis of the IFS in accordance with a preferred embodiment of the present invention. It should be noted that biological tissues are turbid media in which the predominance of light scattering unavoidably entangles the effects of absorption and fluorescence. The interplay of absorption and scattering can substantially distort the measured fluorescence. Therefore, it is important to extract the intrinsic fluorescence from the measured tissue fluorescence. The intrinsic fluorescence is defined as the fluorescence that is due only to fluorophores, without interference from the absorbers and scatterers that are present in the tissue. The greatest distortion of fluorescence spectra occurs for emission near 420 nm where hemoglobin absorbs strongly. Removal of such distortion is particularly important for ultraviolet excitation wavelengths, which have been shown to contain important diagnostic information.

In step 410 the input data is analyzed using the information from the reflectance fit provided by the Zonios model. The inputs include $\mu_s'(\lambda), \mu_\alpha(\lambda)$, fluorescence $F(\lambda)$ and $R_{obs}$; wherein $R_{obs}$ is the observed white light reflectance. Data is also analyzed using a method based on photon-migration theory referred to hereinafter as the Zhang model. The Zhang model is an improvement over the model described in U.S. Pat. No. 5,452,723 entitled "Calibrated Spectrographic Imaging" issued on Sep. 26, 1995, the entire contents of which being incorporated herein by reference. The Zhang model is described in an article entitled, "Turbidity-free fluorescence spectroscopy of biological tissue," by Zhang et al., and published in Optics Letter, Vol. 25, No. 19, Oct. 1, 2000, the entire contents of which being incorporated herein by reference. The Zhang model is based on the fact that when reflectance and fluorescence are collected from a given tissue site with the same probe, absorption and scattering distort fluorescence and reflectance spectra similarly, because the diffusely reflected and the fluorescence photons traverse similar paths.

In a preferred embodiment, the fluorescence intensity of the medium can be modeled as $$F_{xm} = \frac{I_x}{h\nu_x}\left[\sum_{n=l}^{x}\sum_{i=1}^{n-l}\rho_{ni}\alpha_x^i\left(\frac{\mu_{ix}}{\mu_{\alpha x}-\mu_{sx}}\phi_{xm}\right)\alpha_m^{n-i-l}\right]h\nu_m \quad (1)$$

where $I_x$ denotes the excitation intensity, $\phi_{xm}$ is the fluorescence quantum yield, in which the subscripts x and m denote evaluation of the corresponding quantities at excitation frequency $\nu_x$ and emission frequency $\nu_m$, $\rho_{ni}$ denotes the fluorescence escape probability for the fluorescence rates, $\alpha$ is $\mu_s/(\mu_\alpha+\mu_s)$ and represents the fraction of photons not absorbed during each interaction event and can be considered the photon weight reduction factor for that event. Consequently, the expression in brackets has the meaning of fluorescence photons per excitation photon. After the photon transverses the first i absorption–scattering nodes and experiences propagation loss, its weight becomes $\alpha_x^i$ for each incident excitation photon. For each excitation photon arriving at the (i+1)th node, $\mu_{fx}(\mu_{\alpha x}+\mu_{sx})$ photons are absorbed by the fluorophore. For each photon absorbed by the fluorophore, $\phi_{xm}$ fluorescence photons are generated. The propagation loss of the fluorescence photons is accounted for by the factor $\alpha_m^{n-i-l}$.

For a dilute, optically thin ($\mu_{fx}l \ll 1$) sample of thickness l, with the same amount of fluorophore but without other absorbers and scatterers, one obtains the following intrinsic fluorescence, $$f_{xm} = (I_x/h\nu_x)\mu_{fx}l\phi_{xm}h\nu_m \quad (2)$$

The fluorescence expression in equation 1 can be expressed in terms of reflectance with the help of the following:

$$R = \sum_{n=1}^{x} \alpha^n \rho_n = \frac{k\alpha\exp(-\beta)}{1-\alpha\exp(-\beta)} \qquad (3)$$

where R is the reflectance of the homogeneous medium of scatterers and absorbers. The result can be combined with equation 2 to obtain the relationship among intrinsic fluorescence spectrum $f_{xm}$, experimentally measured fluorescence spectrum $F_{xm}$, and reflectance spectrum $R_m$:

$$f_{xm} = \frac{F_{xm}}{\frac{1}{\mu_{sx}l}\left(\frac{R_{ox}R_{om}}{\epsilon_x \epsilon_m}\right)^{1/2}\frac{R_x}{R_{ox}}\left(\frac{R_m}{R_{om}}+\epsilon_m\right)} \qquad (4)$$

wherein $R_o$ is the reflectance in the absence of absorption and $\epsilon=\exp\beta-1$ where $\beta$ is a parameter independent of the number of steps n but dependent on the scattering properties of the medium, and $\mu_s$ are the scattering coefficients of the tissue.

Equation 4 holds for a probe of arbitrary delivery—collection geometry, as long as the fluorescence and reflectance are measured with the same probe: note that $R_o$ is a function of wavelength. Note that Equation 4 can be used to extract an intrinsic fluorescence excitation—emission matrix (EEM) from an experimentally measured fluorescence EEM. When the medium contains multiple fluorophores, one need only replace every occurrence of $\mu_{fx}\phi_{xm}$ in equations 1 and 2 with a summation of this quantity over all fluorophores. Doing so results in the same expression as in equation 4.

In step 420 the IFS($R_{obs}$fit($\lambda$)) is obtained. A biochemical decomposition process may then be performed per step 430. The biochemical decomposition process may be a linear decomposition process based on the IFS and provides a quantitative measure of the spectra. Further a principal component analysis (PCA) analysis may also be performed per step 440.

Figure 17A:
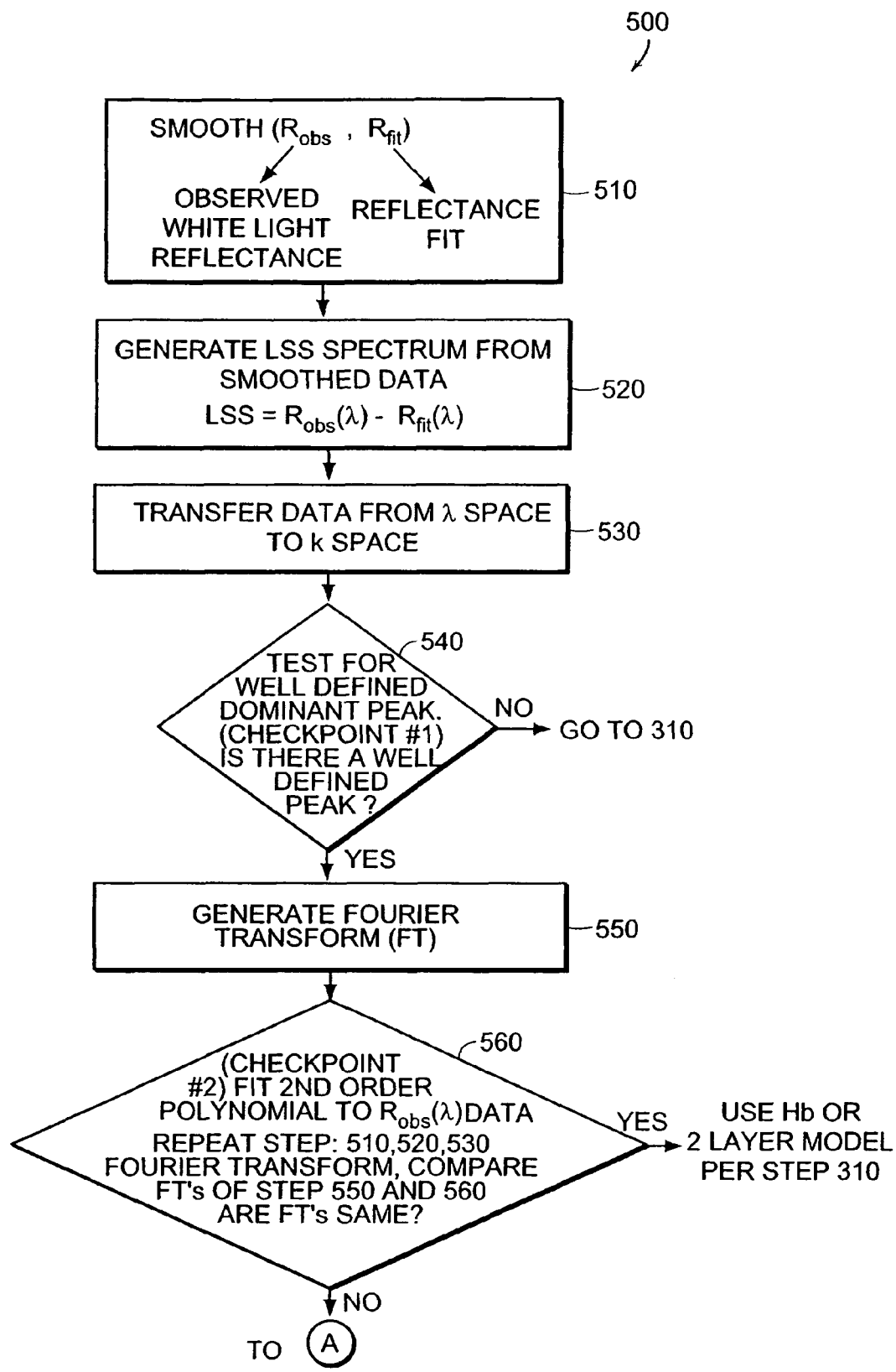
FIGS. 17A and 17B illustrate a flow chart detailing the analysis of the light scattering spectrum (LSS) in accordance with a preferred embodiment of the present invention.
Figure 17B:
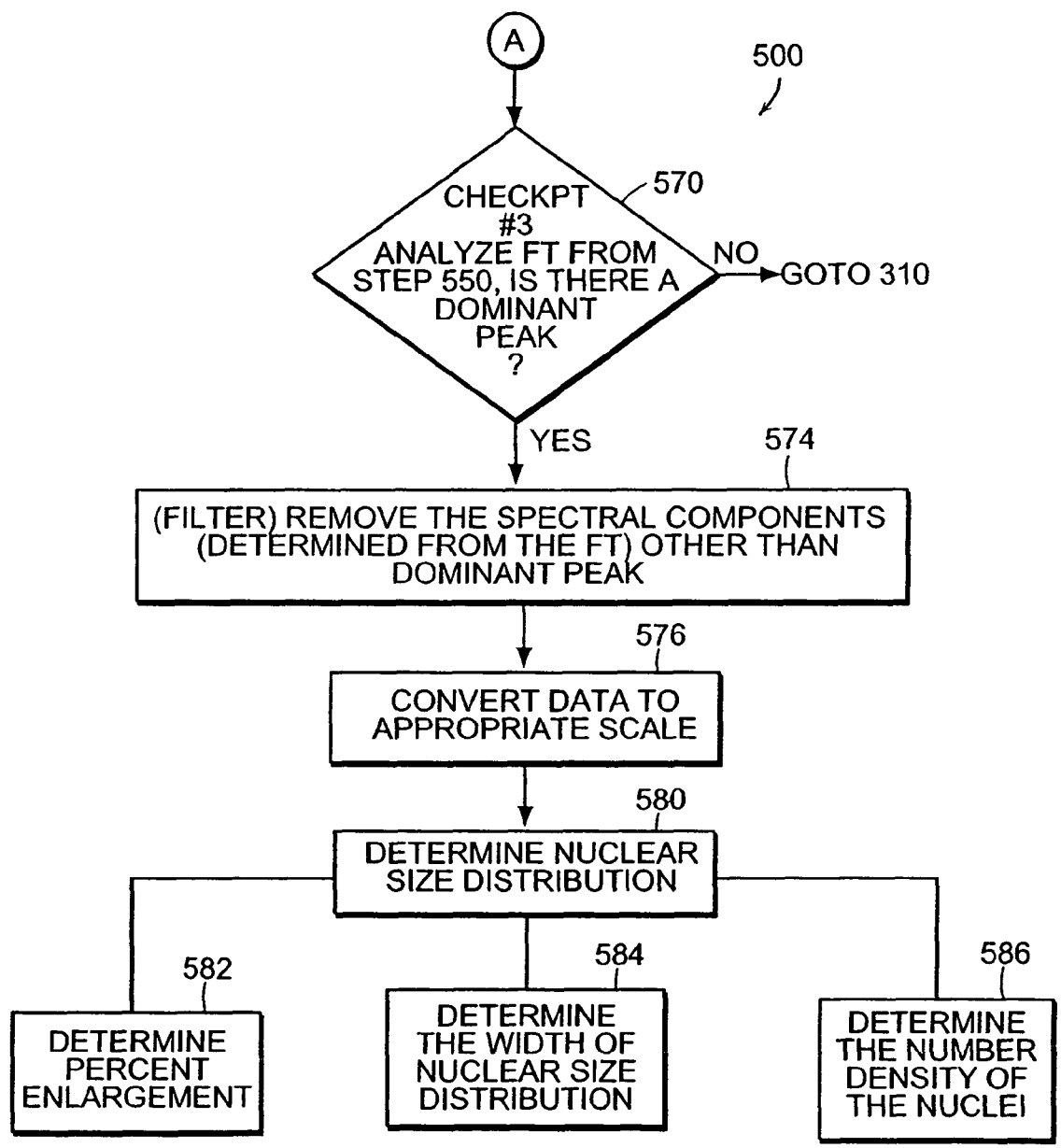

FIGS. 17A and 17B are flow charts detailing the analysis of LSS in accordance with a preferred embodiment of the present invention. The analysis begins with step 510 wherein the observed white light reflectance curve ($R_{obs}(\lambda)$) and the reflectance fit curve ($R_{fit}(\lambda)$) are smoothed. A moving window average smoothing process may be used in a preferred embodiment. An LSS spectrum is generated per step 520 from the smoothed data wherein the LSS spectrum is indicative of the difference between the observed white light reflectance and the reflectance fit (LSS spectrum=$R_{obs}(\lambda)-R_{fit}(\lambda)$). The LSS spectrum is wavelength dependent. The data is then transferred from wavelength ($\lambda$) space to wavenumber (k) space in step 530. A first test is then performed per step 540 wherein it is determined if there is a well defined peak in the spectrum in Fourier space. Only if there is a well defined peak a Fourier transform is estimated, otherwise a reliable diagnosis cannot be provided. In a preferred embodiment the test for the presence of a well-defined peak may include, for example, using a sine Fourier transform $$\int_{k=min}^{k=max}\left(\frac{R(k)}{\overline{R}(k)}-1\right)\mathrm{Sin}kl dk.$$

If a well-defined peak is present, the process follows to step 550 where a Fourier transform (FT) is generated. However, if there is a lack of a well defined peak, the process returns to step 310. The process then enters step 560 which functions as a second test or checkpoint wherein the hemoglobin absorption features are accounted for. The second order polynomial is fit to the $R_{obs}(\lambda)$ data. Steps 510, 520 and 530 are then repeated if the fit is not accurate. A Fourier transform is then performed to compare the resulting FT's from step 550 and step 560. It is then determined if the FT's are the same. If they are different, the process proceeds to step 570. If the FT's are the same however, another hemoglobin or a two layer model, without limitation, is used such as described with respect to the DRS analysis in FIG. 15.

In step 570, a third test or checkpoint is performed by analyzing the FT from step 550 and ascertaining the presence or absence of a dominant peak. If no dominant peak is present then the process returns to step 310 in the DRS analysis as the hemoglobin absorption parameter is then probably an artifact. If a dominant peak exists then spectral components other than the dominant peak are removed such as by filtering high frequency components per step 574.

The data is converted to an appropriate scale per step 576 by, for example, multiplying by an overall scaling constant to normalize the result. The nuclear size distribution is determined in step 580. The determination may include the determination of the percent enlargement of the nuclear size per step 582. The determination of the nuclear size distribution may also include the determination of the width of the nuclear size distribution per step 584. Further, determination of the nuclear size distribution may include the determination of the number density of the nuclei per step 586.

Figure 18:
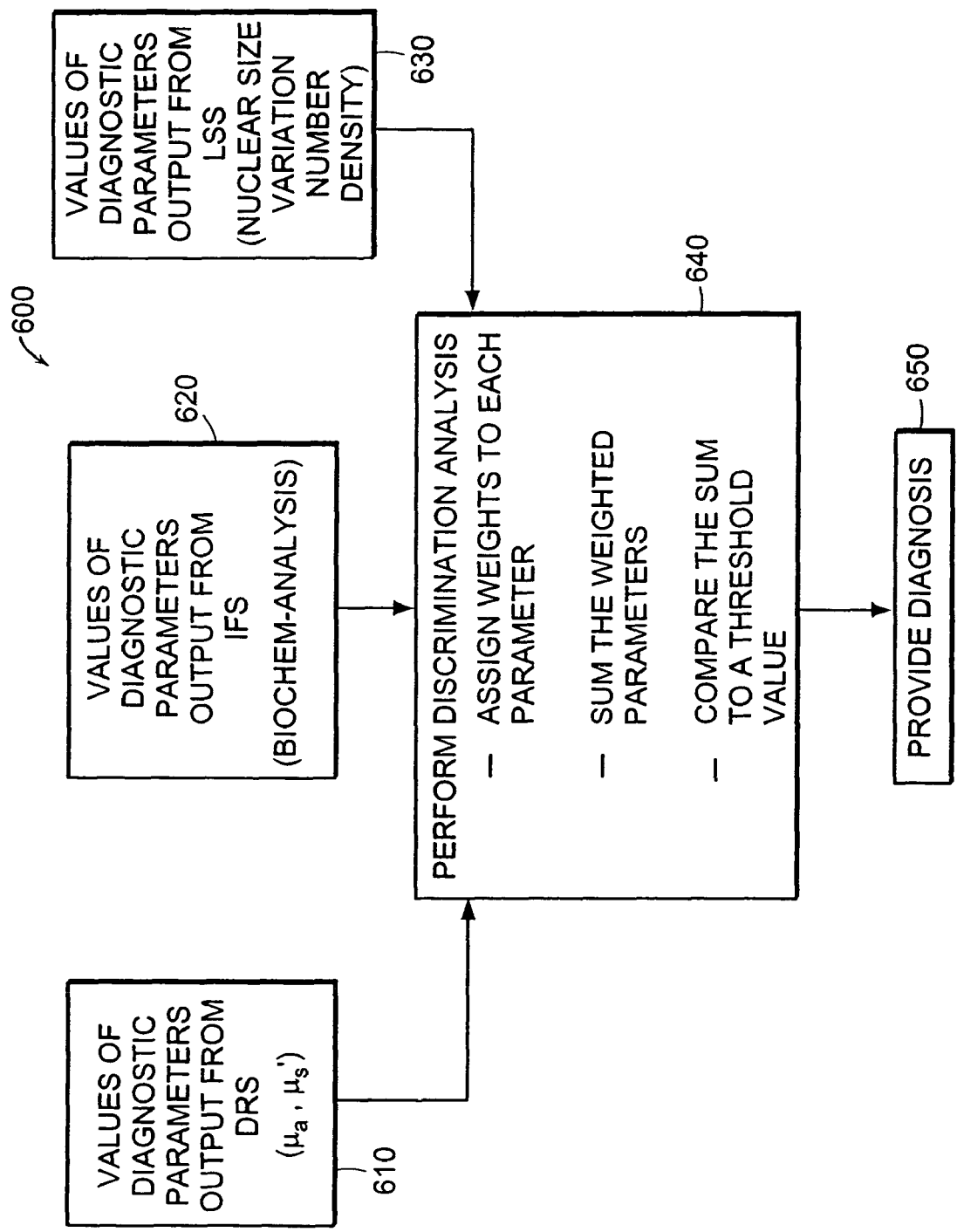
FIG. 18 illustrates the tri-modal system analysis in accordance with a preferred embodiment of the present invention.

FIG. 18 illustrates a preferred embodiment of a tri-modal system (TMS) analysis in accordance with the present invention. The TMS analysis includes step 610 of at least one of taking values of diagnostic parameters output from the DRS analysis ($\mu_a(\lambda)$ and $\mu_s'(\lambda)$), values of diagnostic parameters output from IFS analysis, for example, but not limited to, bio-chemical analysis per step 620 and values of diagnostic parameters output from the LSS analysis, for example, without limitation, nuclear size distribution, size variation, standard deviation and number density per step 630 and performing a discrimination analysis in step 640. In a preferred embodiment the discrimination analysis may include, for example, but without limitation, Fisher discrimination analysis which includes assigning weights to each parameter, summing the weighted parameters and comparing the sum to a threshold value. The results of the TMS analysis are provided as a TMS diagnosis in step 650. The TMS diagnosis includes the assessment about the presence or absence of non-dysplastic tissue, high-grade dysplastic tissue and dysplastic tissue.

Figure 19:
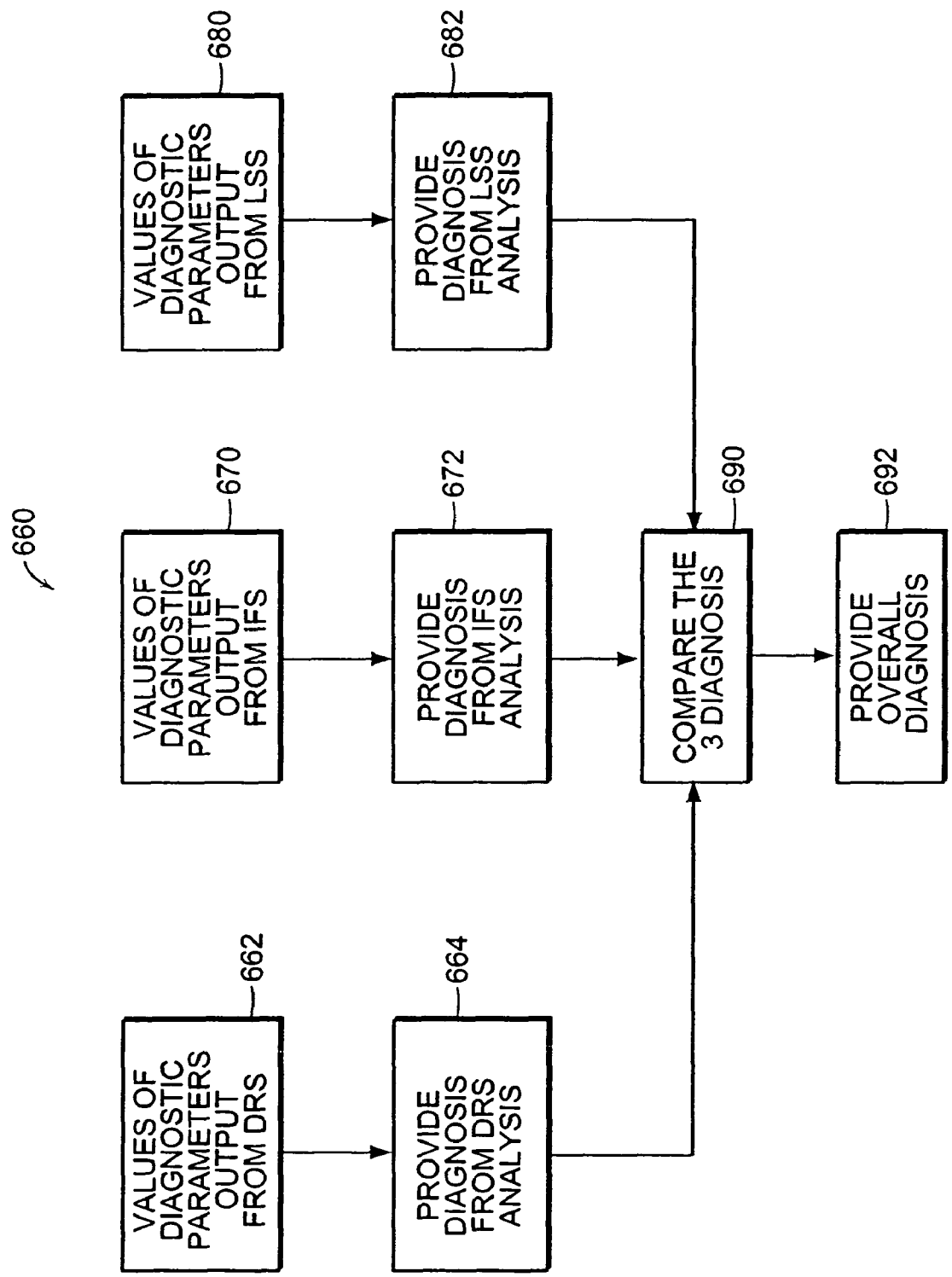
FIG. 19 illustrates an alternate preferred embodiment of a tri-modal system analysis in accordance with the present invention.

FIG. 19 is an alternate preferred embodiment of a TMS analysis in accordance with the present invention. In this preferred embodiment a diagnosis from each modality of spectroscopy is provided individually and compared before providing an overall diagnosis. The values of the diagnostic parameters output from the DRS analysis, for example, $\mu_s'(\lambda)$, in step 662 are used to provide the diagnosis from the DRS analysis per step 664. For example, the slope and intercept data values are determined and compared to threshold values to determine the tissue characteristics. Similarly, the values of the diagnostic parameters output from IFS analysis in step 670 are used to provide a diagnosis commensurate with the IFS analysis in step 672. For example, the contribution of, but not limited to, NADH and/or collagen, and/or porphyrin, to the IFS spectrum are compared to threshold values to provide the diagnosis from the IFS analysis. The values of the diagnostic parameters output from the LSS analysis in step 680 are in turn used to provide a diagnosis from the LSS analysis in step 682. The diagnosis from the LSS analysis includes, for example, the comparison of at least one nuclear size characteristic, such as, nuclear size expressed as a percent enlargement, number density, size variation, width of distribution versus crowding to threshold values. Depending upon the tissue and its location, a combination of two or more nuclear size characteristics may be compared to corresponding threshold values to provide a diagnosis from the LSS analysis.

The three diagnoses, specifically the diagnosis from the DRS analysis, the IFS analysis and the LSS analysis, are compared in step 690. An overall diagnosis is provided from this comparison in step 692. The overall diagnosis may be derived from two similar individual diagnoses, for example, a similar diagnosis from the IFS and LSS analyses. Different permutations and combinations of similar diagnoses may be used in preferred embodiments.

It will be apparent to those of ordinary skill in the art that methods involved in the system of fluorescence, reflectance and light scattering spectroscopy for measuring tissue characteristics may be embodied in a computer program product that includes a computer usable medium. For example, such as, a computer usable medium can include a readable memory device, such as a hard drive device, CD-ROM, a DVD-ROM, or a computer diskette, having computer readable program code segments stored thereon. The computer readable medium can also include a communications or transmission medium, such as, a bus or a communication link, either optical, wired or wireless having program code segments carried thereon as digital or analog data signals.

While this invention has been particularly shown and described with references to preferred embodiments thereof, it will be understood by those skilled in the art that various changes in form and details may be made therein without departing from the scope of the invention encompassed by the appended claims.

The claims should not be read as limited to the described order or elements unless stated to that effect. Therefore, all embodiments that come within the scope and spirit of the following claims and equivalents thereto are claimed as the invention.

What is claimed:

1. A method of measuring spectral data to detect cancerous tissue comprising:
    inserting a fiber optic probe within an endoscope channel, the endoscope being inserted within a body cavity or lumen, the fiber optic probe having a central light delivery optical fiber and a plurality of light collection optical fibers that surround the central light delivery optical fiber, the probe collecting fluorescent light and reflected light from the tissue at a plurality of wavelengths;
    illuminating tissue with light from a broadband light source optically coupled to the central light delivery optical fiber and a laser light source optically coupled to the central delivery optical fiber such that a selected region of tissue is illuminated;
    detecting the collected fluorescent light and reflected light with a detector that is optically coupled to proximal ends of the collection optical fibers;
    processing detected fluorescent light and detected reflected light with a data processor to form an intrinsic fluorescence spectrum and a diffuse reflectance spectrum; and
    determining a characteristic of the tissue using the data processor that processes the intrinsic fluorescence spectrum and the diffuse reflectance spectrum, in combination, to detect cancerous tissue.

2. The method of claim 1 further comprising using the intrinsic fluorescence spectrum to determine one or more components of the tissue.

3. The method of claim 1 further comprising using the diffuse reflectance spectrum to determine a size of a structure within the tissue.

4. The method of claim 3 wherein the using step further comprises generating a lookup table with different sizes of scatterers.

5. The method of claim 1 further comprising measuring a periodic component of the detected light to provide a scattered light representation.

6. The method of claim 1 further comprising analyzing the diffuse reflectance spectrum and a light scattering spectrum.

7. The method of claim 6 further comprising transforming the light scattering spectrum and removing spectral components to determine size distribution of a tissue component.

8. The method of claim 1 wherein the method of measuring spectral data further comprises calibrating with a reflectance standard and a fluorescence standard.

9. The method of claim 1 further comprising processing the intrinsic fluorescence spectrum, the diffuse reflectance spectrum and a light scattering spectrum to determine a characteristic of the tissue.

10. The method of claim 1 wherein the determining step further comprises performing discriminate analysis to diagnose the tissue.

11. The method of claim 1 further comprising using the diffuse reflectance spectrum to obtain a plurality of scattering coefficient values.

12. The method of claim 1 further comprising determining a plurality of biochemical components of the tissue using the detected fluorescence.

13. The method of claim 1 further comprising determining weight coefficients from an analysis of the detected fluorescence light and the detected reflected light.

14. An apparatus for detecting cancerous tissue comprising:
    a broadband light source that illuminates a region of interest in tissue to be measured with incident light;
    a laser light source;
    a fiber optic probe that collects reflected light and fluorescent light from a body tissue surface at a plurality of wavelengths, the probe having a central light delivery optical fiber that is optically coupled to the laser light source and the broadband light source such that a selected tissue region can be illuminated with the laser light source and the broadband light source, and a plurality of light collection optical fibers surrounding the central light delivery fiber;
    a detector system optically coupled to the collection optical fibers that detects the collected light and provides fluorescence data and reflected light data at a plurality of wavelengths; and
    a data processor that processes the fluorescence data and the reflected light data to provide an intrinsic fluorescence spectrum and a diffuse reflectance spectrum, the intrinsic fluorescence spectrum and the diffuse reflectance spectrum being processed in combination to identify cancerous tissue in the region of interest.

15. The apparatus of claim 14 wherein the broadband light source generates light in a range of 330-700 nm.

16. The apparatus of claim 14 wherein the fiber optic probe has an optical shield at a distal end that couples light from the broadband light source and the laser light source to the tissue.

17. The apparatus of claim 14 wherein the probe is adapted for insertion into a working channel of an endoscope.

18. The apparatus of claim 14 further comprising a fast excitation-emission matrix instrument including the laser light source that illuminates tissue at a plurality of excitation wavelengths between 337 nm and 620 nm.

19. The apparatus of claim 14 further comprising a spectrograph optically coupled to proximal ends of the collection optical fibers.

20. The apparatus of claim 14 wherein the probe comprises six collection optical fibers within a probe that is 5 mm or less in diameter.

21. A method for detecting cancerous tissue comprising:
acquiring a fluorescence spectrum with a fiber optic probe positioned to illuminate a body tissue surface, the fiber optic probe having a central light delivery optical fiber that is optically coupled at a proximal end to a laser light source and a plurality of light collection optical fibers surrounding the central delivery optical fiber;
acquiring a reflectance spectrum with the fiber optic probe, the central delivery fiber being optically coupled at the proximal end to a broadband light source;
processing the fluorescence spectrum and the reflectance spectrum with a data processor to provide an intrinsic fluorescence spectrum and a diffuse reflectance spectrum; and
processing the intrinsic fluorescence spectrum and the diffuse reflectance spectrum, in combination, with the data processor to determine a biophysical tissue characteristic and thereby identify cancerous tissue.

22. The method of claim 21 further comprising determining a size of a structure within the tissue.

23. The method of claim 22 wherein the structure is the nuclei of epithelial cells in the tissue.

24. The method of claim 22 wherein the determining step further comprises generating a look-up table with different sizes of scatterers.

25. The method of claim 21 further comprising measuring a periodic component of the acquired reflectance spectrum.

26. The method of claim 21 further comprising calibrating a detector optically coupled to the probe using a reflectance standard and a fluorescence standard.

27. The method of claim 21 further comprising using the reflectance spectrum and the fluorescence spectrum to obtain the intrinsic fluorescence spectrum.

28. The method of claim 21 further comprising acquiring and transforming a light scattering spectrum and removing spectral components to determine size distribution of a tissue component.

29. The method of claim 21 wherein the determining step further comprises performing discriminate analysis for providing a real-time diagnosis for the tissue.

30. The method of claim 21 further comprising determining a plurality of scattering coefficient values and associating the plurality of scattering coefficient values with a plurality of different tissue regions.

31. The method of claim 21 further comprising detecting light collected by the collection optical fibers with a detector that is optically coupled to proximal ends of the collection optical fibers.

* * * * *